United States Patent
Kawaguchi

(10) Patent No.: US 11,160,575 B2
(45) Date of Patent: Nov. 2, 2021

(54) TREATMENT INSTRUMENT

(71) Applicant: OLYMPUS CORPORATION, Hachioji (JP)

(72) Inventor: Yuki Kawaguchi, Koshu (JP)

(73) Assignee: OLYMPUS CORPORATION, Tokyo (JP)

( * ) Notice: Subject to any disclaimer, the term of this patent is extended or adjusted under 35 U.S.C. 154(b) by 202 days.

(21) Appl. No.: 16/209,026

(22) Filed: Dec. 4, 2018

(65) Prior Publication Data

US 2019/0105068 A1 Apr. 11, 2019

Related U.S. Application Data

(63) Continuation of application No. PCT/JP2016/067685, filed on Jun. 14, 2016.

(51) Int. Cl.
| | |
|---|---|
| *A61B 17/29* | (2006.01) |
| *A61B 17/064* | (2006.01) |
| *A61B 17/00* | (2006.01) |

(52) U.S. Cl.
CPC ............ *A61B 17/29* (2013.01); *A61B 17/064* (2013.01); *A61B 2017/0042* (2013.01);
(Continued)

(58) Field of Classification Search
CPC .................. A61B 17/29; A61B 17/064; A61B 2017/00314; A61B 2017/2929;
(Continued)

(56) References Cited

U.S. PATENT DOCUMENTS 5,383,888 A 1/1995 Zvenyatsky et al.
2007/0287993 A1* 12/2007 Hinman ................. A61B 17/29
606/1
(Continued)

FOREIGN PATENT DOCUMENTS

CN 101909526 A 12/2010
JP 2011-92743 A 5/2011
(Continued)

OTHER PUBLICATIONS

Oct. 8, 2019 Office Action issued in Japanese Patent Application No. 2018-523080.
(Continued)

*Primary Examiner* — George J Ulsh
*Assistant Examiner* — Rachel S Highland
(74) *Attorney, Agent, or Firm* — Oliff PLC

(57) ABSTRACT

In a treatment instrument, a shaft is rotatable around a predetermined rotation axis relative to the housing, and an end effector is bendably or curvably attached to the shaft. In the treatment instrument, an interlocking member is provided independently of the shaft, and a receiver is provided in such a manner that rotation of the receiver relative to the housing is restricted or that rotation of the receiver relative to the shaft is restricted. The interlocking member moves in conjunction with bending or curving movement of the end effector so that the receiver engages with the interlocking member, thereby preventing rotation of the shaft around the predetermined rotation axis.

10 Claims, 11 Drawing Sheets

(52) U.S. Cl.
CPC .............. *A61B 2017/00314* (2013.01); *A61B 2017/00327* (2013.01); *A61B 2017/2901* (2013.01); *A61B 2017/293* (2013.01); *A61B 2017/2912* (2013.01); *A61B 2017/2929* (2013.01); *A61B 2017/2936* (2013.01); *A61B 2017/2937* (2013.01); *A61B 2017/2946* (2013.01)

(58) Field of Classification Search
CPC .. A61B 2017/0042; A61B 2017/00327; A61B 2017/293; A61B 2017/2901; A61B 2017/2912; A61B 2017/2936; A61B 2017/2937; A61B 2017/2946
See application file for complete search history.

(56) References Cited

U.S. PATENT DOCUMENTS

| | | |
|---|---|---|
| 2009/0171147 A1 | 7/2009 | Lee et al. |
| 2011/0238108 A1 | 9/2011 | Peine et al. |
| 2012/0234893 A1* | 9/2012 | Schuckmann ... A61B 17/07207 227/175.2 |
| 2013/0317522 A1 | 11/2013 | Nishizawa et al. |

FOREIGN PATENT DOCUMENTS

| | | |
|---|---|---|
| JP | 2013-176651 A | 9/2013 |
| WO | 2010/126129 A1 | 11/2010 |
| WO | 2013/35870 A1 | 3/2013 |

OTHER PUBLICATIONS

Sep. 29, 2020 Office Action issued in Chinese Patent Application No. 201680086831.2.

Sep. 13 2016 International Search Report issued in International Patent Application No. PCT/JP2016/067685.

Dec. 18, 2018 International Preliminary Report on Patentability issued in International Patent Application No. PCT/JP2016/067685.

* cited by examiner

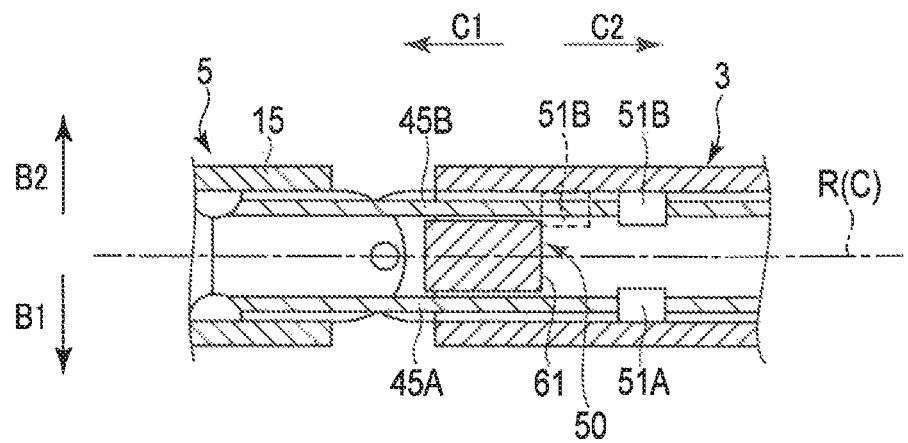
F I G. 9A
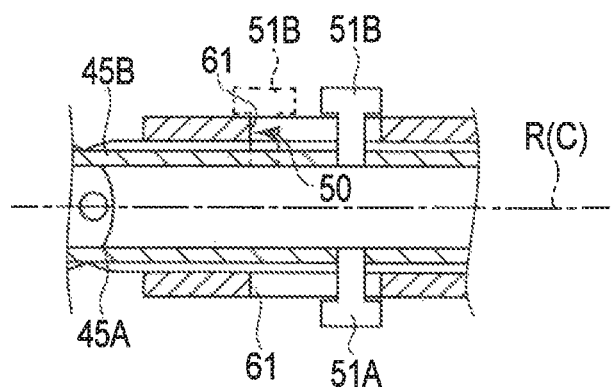
F I G. 9B

TREATMENT INSTRUMENT

CROSS-REFERENCE TO RELATED APPLICATIONS

This is a Continuation Application of PCT Application No. PCT/JP2016/067685, filed Jun. 14, 2016, the entire contents of which are incorporated herein by reference.

BACKGROUND OF THE INVENTION

1. Field of the Invention

The present invention relates to a treatment instrument to treat a treatment target with an end effector.

2. Description of the Related Art

U.S. Pat. No. 5,383,888 discloses a treatment instrument in which an end effector to treat a treatment target is provided on a distal portion of a shaft. In this treatment instrument, a shaft is coupled to a holdable housing, and a handle is opened or closed with respect to a grip of the housing, by which a pair of gripping pieces is opened or closed. By the closed gripping pieces, a treatment target such as living tissue is gripped between the gripping pieces. A rotating member (a rotating knob) that is a part of the shaft is attached to the housing to be rotatable about the central axis of the shaft. When an operation force for rotating the rotating member is applied, the shaft and the end effector rotate together with the rotating member about the central axis of the shaft as a predetermined rotation axis relative to the housing. As a result, the angular position of the end effector around the predetermined rotation axis changes. Furthermore, in this treatment instrument, the end effector is bent relative to the shaft (the central axis of the shaft) based on an operation at the bending operation section (a wing member) provided on the housing.

BRIEF SUMMARY OF THE INVENTION

According to one aspect of the invention, a treatment instrument includes that: a holdable housing; a shaft rotatable around a predetermined rotation axis relative to the housing; an end effector attached to a distal portion of the shaft, and bendable or curvable relative to the shaft; and a locking mechanism including: an interlocking member provided independently of the shaft and configured to move in conjunction with bending movement or curving movement of the end effector relative to the shaft; and a receiver provided in such a manner that rotation of the receiver relative to type housing is restricted or in such a manner that rotation of the receiver relative to the shaft is restricted, the receiver being configured to engage with the interlocking member while the end effector is bent or curved relative to the shaft, thereby preventing rotation of the shaft around the predetermined rotation axis.

According to one another aspect of the invention, a treatment instrument includes that: a holdable housing; a shaft rotatable around a predetermined rotation axis relative to the housing; an end effector attached to a distal portion of the shaft, and bendable or curvable relative to the shaft; a bending drive member configured to transmit an operation force for bending or curving the end effector; an interlocking member provided to move together with the bending drive member; and a receiver configured to engage with the interlocking member so as to prevent the shaft from rotating around the predetermined rotation axis while the end effector is bent or curved.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9A is a cross-sectional view schematically showing an internal configuration of a shaft according to a modification of the second embodiment;

FIG. 9B is a cross-sectional view schematically showing an internal configuration of a shaft according to another modification of the second embodiment;

DETAILED DESCRIPTION OF THE INVENTION

First Embodiment

Figure 1:
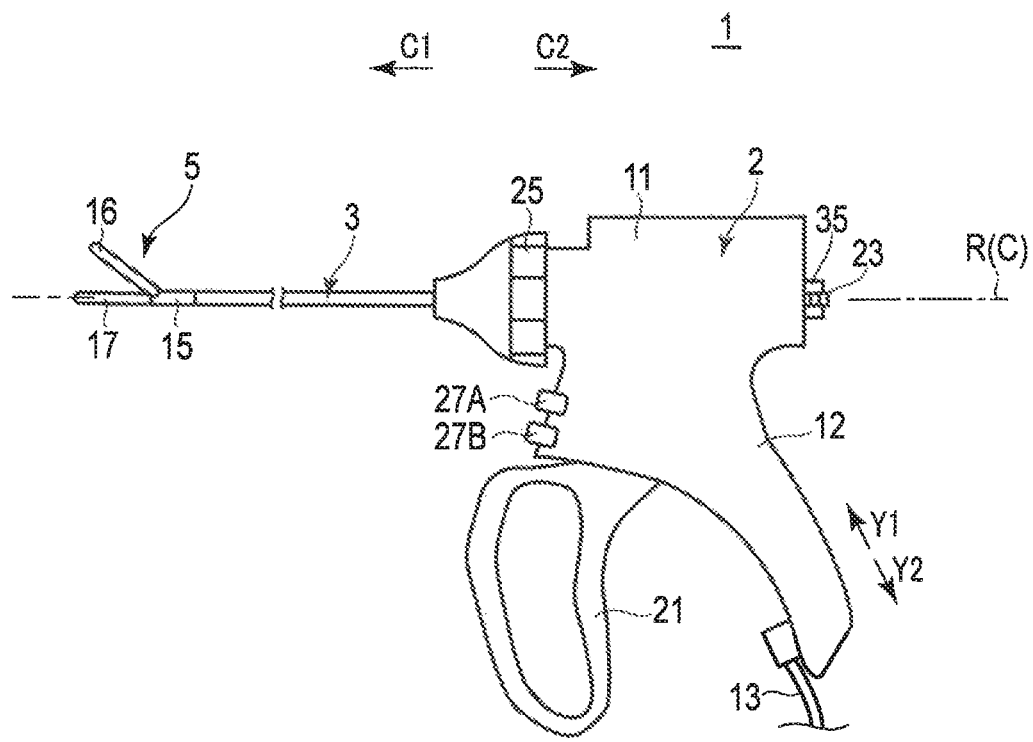
FIG. 1 is a schematic diagram showing a treatment instrument according to a first embodiment.

A first embodiment of the present invention will be described with reference to FIGS. 1 to 5. FIG. 1 is a diagram showing a treatment instrument (a gripping treatment instrument) 1 of the present embodiment. As shown in FIG. 1, the treatment instrument 1 has a longitudinal axis C. Herein, one side of the direction along the longitudinal axis C is defined as a distal side (the arrow C1 side), and the side opposite of the distal side is defined as a proximal side (the arrow C2 side).

The treatment instrument 1 includes a holdable housing 2, a shaft (a sheath) 3 coupled to the housing 2 from the distal side, and an end effector 5 attached to a distal portion of the shaft 3. The shaft 3 extends along the longitudinal axis C from the proximal side to the distal side, and the central axis of the shaft 3 is approximately coaxial with the longitudinal axis C. In the shaft 3, the side approaching the housing 2 is the proximal side, and the side approaching the end effector 5 is the distal side. The shaft 3 is rotatable around the central axis relative to the housing 2. In other words, the central axis of the shaft 3 is a predetermined rotation axis R of the rotation of the shaft 3 relative to the housing 2.

The housing 2 includes a housing main body 11 extending along the longitudinal axis C (the predetermined rotational axis R of the shaft 3), and a grip (a fixed handle) 12 extending from the housing main body 11 along a direction intersecting with the predetermined rotation axis R (the direction indicated by arrow Y1 and arrow Y2). The grip 12 is provided in a position away from the predetermined rotation axis R (the longitudinal axis C). One end of a cable 13 is connected to the grip 12. The other end of the cable 13 is connected to an energy control device (not shown). Herein, a direction intersecting with (approximately perpendicular to) the longitudinal axis C (the predetermined rotation axis R) and intersecting with (approximately perpendicular to) the extending direction of the grip 12 is defined as a width direction of the housing 2. FIG. 1 is a diagram of the treatment instrument 1 seen from one side of the width direction of the housing 2.

Figure 2:
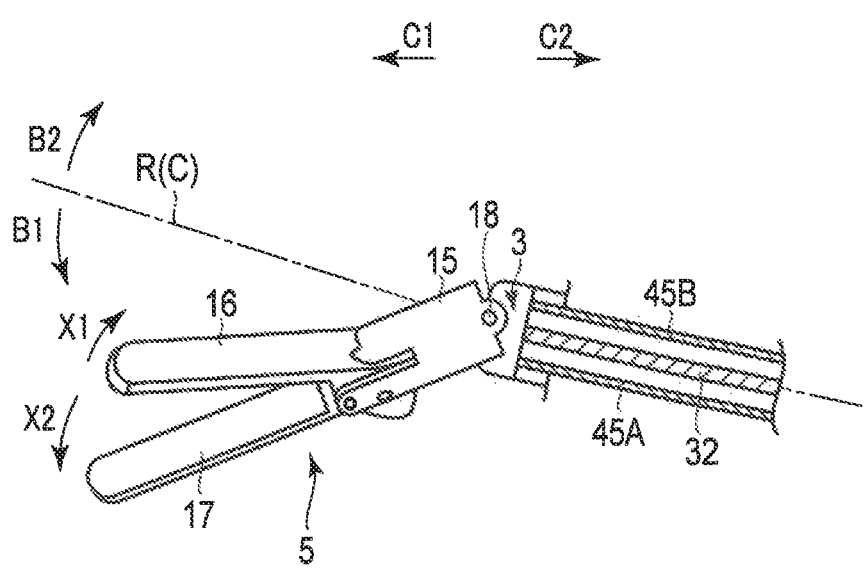
FIG. 2 is a perspective view schematically showing the configuration of an end effector according to the first embodiment.

FIG. 2 is a diagram showing the configuration of the end effector 5. As shown in FIGS. 1 and 2, the end effector 5 is rotatable together with the shaft 3 around the predetermined rotation axis R relative to the housing 2, and is bendable relative to the shaft 3 (the predetermined rotation axis R). The rotation of the end effector 5 changes the angular position of the end effector 5 around the predetermined rotation axis R. The bending direction of the end effector 5 (the direction indicated by arrow B1 and arrow B2) intersects with (is approximately perpendicular to) the predetermined rotation axis R. The end effector 5 includes a relay member 15, a first gripping piece 16, and a second gripping piece 17. The relay member 15 is attached to the distal end of the shaft 3 in a bendable manner relative to the shaft 3. In other words, a bending joint 18 is formed between the shaft 3 and the relay member 15. In the end effector 5, the space between the pair of gripping pieces 16 and 17 can be opened and closed. The opening/closing directions (the directions indicated by arrow X1 and arrow X2) of the gripping pieces 16 and 17 intersect with the predetermined rotation axis R, and intersect with the bending direction of the end effector 5.

In one example, one of the gripping pieces 16 and 17 is integrated with or fixed to the relay member 15, and the other one of the gripping pieces 16 and 17 is pivotably attached to the relay member 15. In another example, both of the gripping pieces 16 and 17 are pivotably attached to the relay member 15. In yet another example, a rod member (not shown) extends from the inside of the relay member 15 toward the distal side, and one of the gripping pieces 16 and 17 is formed of a part of the rod member protruding from the relay member 15 toward the distal side. The other one of the gripping pieces 16 and 17 is pivotably attached to the relay member 15.

A handle (a movable handle) 21 is pivotably attached to the housing 2. The handle 21 pivots relative to the housing 2, so that the handle 21 opens or closes with respect to the grip 12. In other words, the handle 21 is openable/closable relative to the grip 12. In the present embodiment, since the treatment instrument 1 is in a pistol-like shape, the handle 21 is located on the side where the grip 12 is located relative to the predetermined rotation axis R (the longitudinal axis C), and located on the distal side relative to the grip 12. The moving direction of the handle 21 in an opening movement and a closing movement relative to the grip 12 is approximately parallel to the longitudinal axis C. In an example, the handle 21 may be provided on the proximal side relative to the grip 12. In another example, the handle 21 and the grip 12 are provided on the opposite sides from each other with the predetermined rotation axis R being as the center axis, and the moving direction of the opening movement and the closing movement of the handle 21 relative to the grip 12 may be approximately perpendicular to the longitudinal axis C.

A bending dial 23 is attached to the housing 2, as a bending operation input section (an operation input section). For example, by rotating the bending dial 23, an operation of bending the end effector 5 relative to the shaft 3 is input. A rotating member 25 (a rotating knob), which is a part of the shaft 3, is attached to the distal side of the housing main body 11. The shaft 3 is attached to the housing 2 in such a manner that the shaft is inserted into the housing main body 11 from the distal side. The rotating member 25 is fixed to the shaft 3 and rotates together with the shaft 3 and the end effector 5 around the predetermined rotation axis R relative to the housing 2. In the present embodiment, an operation force for rotating the shaft 3, and the end effector 5 about the predetermined rotation axis R is applied to the rotating member 25 as a rotating operation input section.

Operation buttons 27A and 27B are attached to the housing 2. An operation input is performed by pressing each of the operation buttons 27A and 27B. When an operation input is performed by each of the operation buttons 27A and 27B, the treatment instrument 1 is activated in a predetermined activation mode. At this time, for example, similarly to a well-known treatment instrument, one of high-frequency current, ultrasonic vibration, and heat of a heater is applied, as treatment energy, to the treatment target gripped between the gripping pieces 16 and 17, In one example, when the treatment instrument 1 is activated in a predetermined activation mode based on an operation input by either one of the operation buttons 27A and 27B, an electric motor is driven, which may result in a staple being pierced into the treatment target gripped between the gripping pieces 16 and 17.

Figure 3:
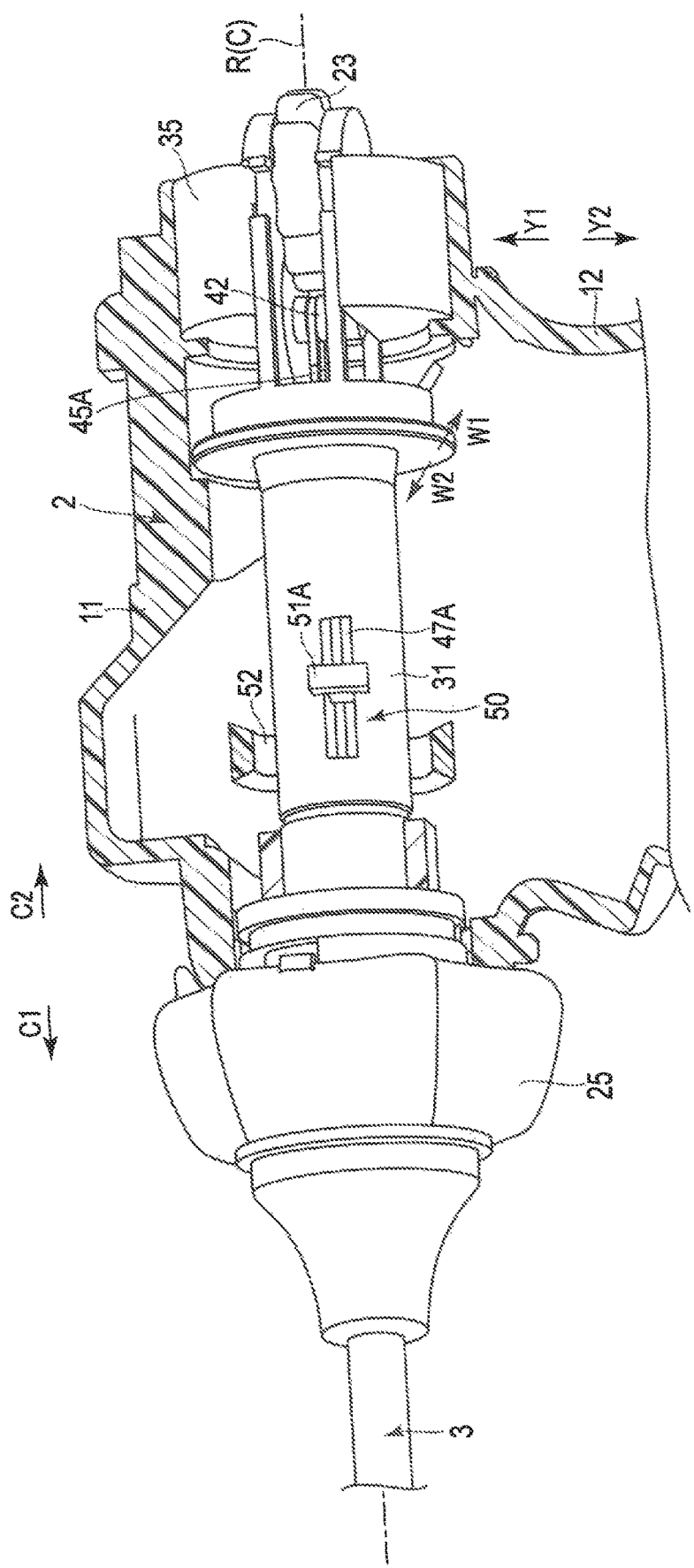
FIG. 3 is a perspective view schematically showing an internal configuration of a housing according to the first embodiment.
Figure 4:
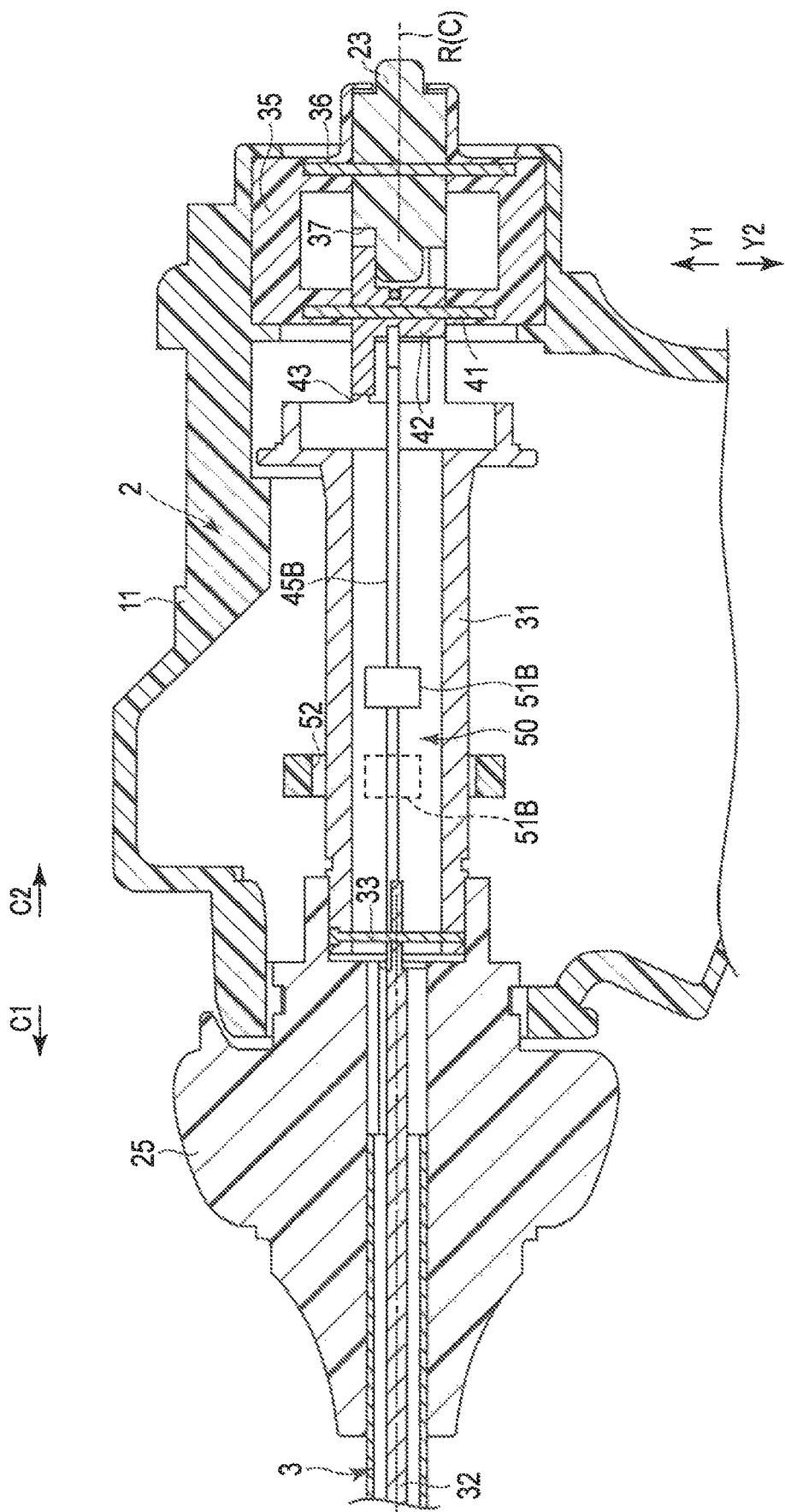
FIG. 4 is a cross-sectional view schematically showing the internal configuration of the housing according to the first embodiment in a cross section approximately perpendicular to the width direction of the housing.
Figure 5:
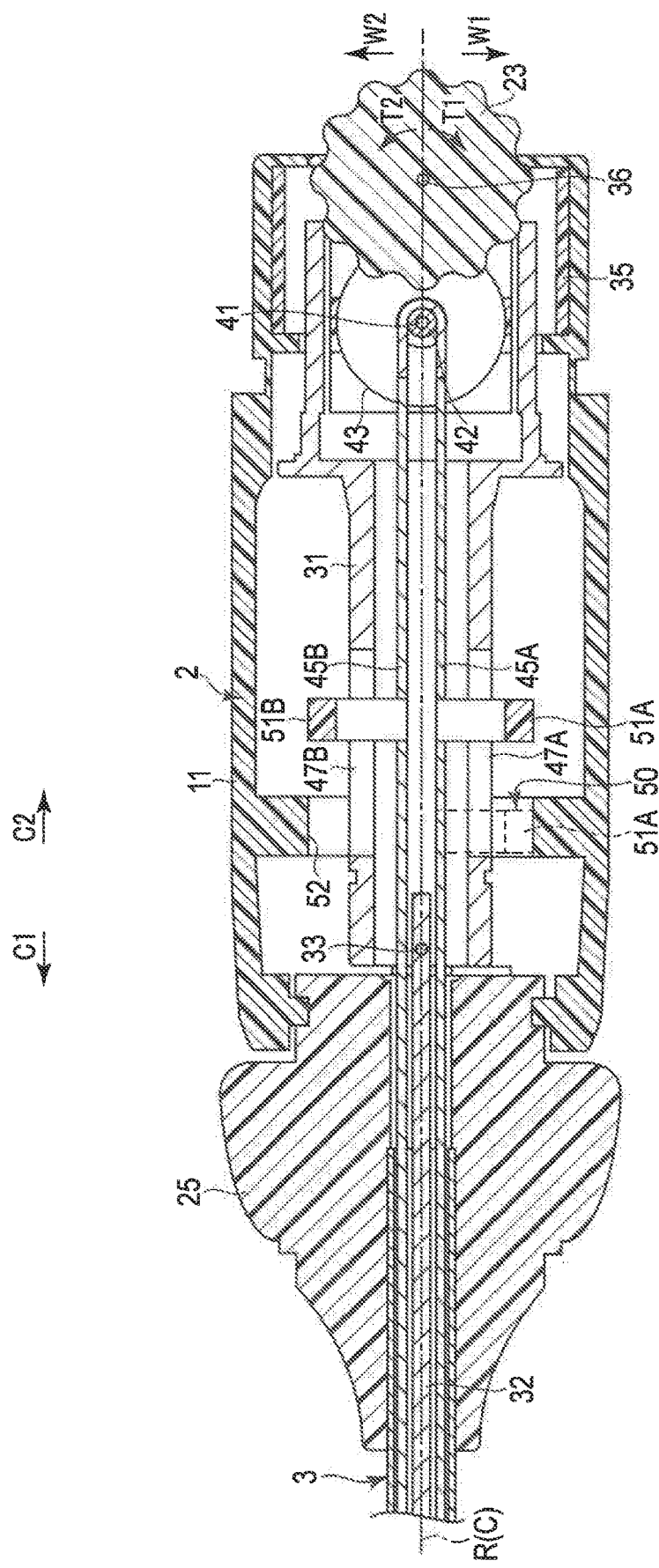
FIG. 5 is a cross-sectional view schematically showing the internal configuration of the housing according to the first embodiment in a cross section approximately parallel to a predetermined rotation axis and approximately parallel to the width direction of the housing.

FIGS. 3 to 5 are diagrams showing the internal configurations of the housing main body 11 of the housing 2 and the rotating member (a rotating knob) 25. FIG. 3 is a perspective diagram. FIG. 4 shows a cross section that is approximately perpendicular to (intersecting with) the width direction of the housing 2 (the directions indicated by arrow W1 and arrow W2). FIG. 5 shows a cross section approximately parallel to the predetermined rotation axis R (the longitudinal axis C) and approximately parallel to the width direction of the housing 2. As shown in FIGS. 3 to 5, inside the housing 2 (the housing main body 11), a tubular movable member 31 is attached to the rotating member 25 from the proximal side (the arrow C2 side). The movable member 31 extends along the predetermined rotation axis R (the longitudinal axis C), and is movable along the predetermined rotation axis R relative to the housing 2 and the shaft 3 (the rotating member 25). However, the rotation of the movable member 31 around the predetermined rotation axis R relative to the shaft 3 is restricted, and the movable member 31 is rotatable together with the shaft 3 and the end effector 5 around the predetermined rotation axis R relative to the housing 2.

Inside the housing 2, the handle 21 is coupled to the movable member 31 via a slider member (not shown), the slider member being arranged on the outer periphery surface of the movable member 31. The movable member 31 is rotatable about the predetermined rotation axis R relative to the handle 21. Also, inside the housing 2, a drive rod 32 as an opening/closing drive member is fixed to the movable member 31 via the connecting member 33. The drive rod 32 extends along the predetermined rotation axis R from the inside of the movable member 31 through the inside of the shaft 3. Since the drive rod 32 is fixed to the movable member 31, when the operation force at the rotating member 25 is applied, the drive rod 32 rotates together with the shaft 3, the end effector 5, and the movable member 31 around the predetermined rotation axis R relative to the housing 2.

The operation force applied to the handle 21 causes the handle 21 to open or close with respect to the grip 12, so that the movable member 31 and the drive rod 32 move along the predetermined rotation axis R (the longitudinal axis C) relative to the shaft 3 and the housing 2. As shown in FIG. 2, one end (the distal end) of the drive rod 32 extending through the inside of the shaft 3 is connected to the end effector 5. By moving the movable member 31 and the drive rod 32 along the predetermined rotation axis R, at least one of the gripping pieces 16 and 17 pivots relative to the relay member 15, and the gripping pieces 16 and 17 open or close relative to each other.

As shown in FIGS. 3 to 5, the bending dial 23 as a bending operation input section (an operation input section) is attached to the housing 2 via a base member 35. In the present embodiment, the base member 35 and the bending dial 23 are installed on the outer surface of the housing main body 11 in the part facing the proximal side. The bending dial 23 is attached to the base member 35 via the supporting shaft 36. The bending dial 23 can rotationally move around the supporting shaft 36 relative to the base member 35. The operation to bend the end effector 5 relative to the shaft 3 is input at the bending dial 23, so that the bending dial 23 rotationally moves around the supporting shaft 36. A gear portion 37 is formed on the bending dial 23 over the entire circumference along the circumferential direction of the supporting shaft 36. In the present embodiment, the gear portion 37 is arranged inside the housing 2 so as not to be exposed to the outside of the housing 2.

A pulley 42 is attached to the base member 35 via the supporting shaft 41. In the present embodiment, the pulley 42 is located inside the housing main body 11. The pulley 42 can rotationally move around the supporting shaft 41 relative to the base member 35. A gear portion 43 is formed on the pulley 42 over the entire circumference along the circumferential direction of the supporting shaft 41. The gear portion 43 engages with the gear portion 37 of the bending dial 23. The bending dial 23 rotationally moves based on the operation input at the bending dial 23, so that the pulley 42 is activated to rotationally move around the supporting shaft 41 relative to the base member 35. As a result, the pulley 42 as an operation force transmitter transmits an operation force for bending the end effector 5 relative to the shaft 3.

The proximal ends (one end) of wires 45A and 45B as bending drive members (drive members) are connected to the pulley 42. The pair of wires 45A and 45B extend along the predetermined rotation axis R (the longitudinal axis C) through the inside of the movable member 31 and the shaft 3. As shown in FIG. 2, the distal ends (the other ends) of the wires 45A and 45B are connected to the relay member 15 of the end effector 5. The pulley 42 as the operation force transmitter rotationally moves, so that the operation force for bending the end effector 5 is transmitted from the pulley 42 to the wires 45A and 45B. As a result, the wires 45A and 45B move along the predetermined rotation axis R (the longitudinal axis C) relative to the shaft 3 and the movable member 31. By the movement of the wires 45A and 45B, the end effector 5 is bent relative to the shaft 3 (the predetermined rotation axis R). In one example, a pair of leaf springs or the like may be provided as bending drive members, instead of the wires 45A and 45S.

In this embodiment, when the bending dial 23 rotationally moves to one side (the arrow T1 side) of the circumferential direction of the supporting shaft 36, the wire 45A moves toward the proximal side (i.e., the wire 45A is pulled), and the wire 45B moves toward the distal side (i.e., the wire 45B is relaxed). As a result, the end effector 5 is bent to one side (the arrow B1 side) of the bending direction relative to the shaft 3 (the predetermined rotation axis R). In contrast, when the bending dial 23 rotationally moves to the other side (the arrow T2 side) of the circumferential direction of the supporting shaft 36, the wire 45B moves toward the proximal side, and the wire 45A moves toward the distal side. As a result, the end effector 5 is bent to the other side (the arrow B2 side) of the bending direction relative to the shaft 3.

In the present embodiment, the pulley 42 forms an operation force transmitter that is activated based on the operation input at the bending dial (the operation input member) 23 so as to transmit the operation force for bending the end effector 5. However, the configuration is not limited thereto. In one example, a plurality of pulleys may form an operation force transmitter that transmits an operation force from the bending dial (the operation inputter) 23 to the wires 45A and 45B (the bending drive members). In another example, one end of the wires 45A and 45B (the bending drive members) may be directly connected to the bending dial (the bending operation input section) 23. In this case, the bending dial 23 as a bending operation input member also functions as an operation force transmitter that transmits an operation force to the wires 45A and 45B.

As shown in FIGS. 3 to 5, inside the housing main body 11, the base member 35 is coupled to the movable member 31 from the proximal side. The movable member 31 is movably coupled to the base member 35 along the predetermined rotation axis R (the longitudinal axis C). However, the rotation of the movable member 31 and the base member 35 around the predetermined rotation axis R relative to each other is restricted. The bending dial 23 and the pulley 42 are rotatable together with the base member 35 around the predetermined rotation axis R relative to the housing 2.

Because of the above-described configuration, when the operation force at the rotating member 25 is applied to rotate the shaft 3 around the predetermined rotation axis R, a rotation drive force around the predetermined rotation axis R is transmitted from the shaft 3 to the bending dial (the bending operation input section) 23 and the pulley (the operation force transmitter) 42 via the movable member 31 and the base member 35. As a result, the bending dial 23 and the pulley 42 rotate together with the shaft 3 (the rotating member 25) and the end effector 5 around the predetermined rotation axis R relative to the housing 2. At this time, the wires (the bending drive members) 45A and 45B connected between the pulley 42 and the end effector 5 also rotate together with the shaft 3, the end effector 5, the bending dial 23, and the pulley 42 around the predetermined rotation axis R.

A pair of slots 47A and 47B that communicates the inside of the movable member 31 with the outside of the movable member 31 are formed on the movable member 31. A pair of interlocking members 51A and 51B is provided inside the housing 2 (the housing main body 11). The interlocking member 51A is inserted into the movable member 31 from the slot 47A, and is fixed to the wire 45A. Similarly, the interlocking member 51B is inserted into the movable member 31 from the slot 47B, and is fixed to the wire 45B. Accordingly, the interlocking members 51A and 51B are provided independently of (separately from) the shaft Each of the interlocking members 51A and 51B protrudes from a corresponding one of the slots 47A and 47B to the outside of the movable member 31.

The slots 47A and 47B are formed in a long hole shape along the predetermined rotation axis R. Accordingly, when the operation force for bending the end effector 5 is transmitted to the wires 45A and 45B to move each of the wires 45A and 45B along the predetermined rotation axis R, the interlocking member 51A moves together with the wire (the drive member) 45A, and the interlocking member 51B moves together with the wire (the drive member) 455. In other words, each of the interlocking members 51A and 51B moves in the corresponding one of the slots 47A and 47B along the predetermined rotation axis R. Therefore, the interlocking members 51A and 51B move in conjunction with the bending movement of the end effector 5 relative to the shaft 3.

The housing 2 (the housing main body 11) is provided with an engaging protrusion (a receiver) 52 protruding toward the inner peripheral side. The engaging protrusion (the receiver) 52 is provided in such a manner that the rotation of the engaging protrusion 52 around the predetermined rotation axis R relative to the housing 2 is restricted. The engaging protrusion (the receiver) 52 may be integrally formed with the housing 2, or may be formed as a separate member from the housing 2. In the present embodiment, the engaging protrusion 52 extends along the circumferential direction of the movable member 31. The interlocking members 51A and 51B can engage with the engaging protrusion (the receiver) 52 inside the housing 2 and outside the movable member 31. However, when the end effector 5 is not bent relative to the shaft 3 (the predetermined rotation axis R) (a neutral state), the interlocking members 51A and 51B are located away from the engaging protrusion 52 in the direction along the predetermined rotation axis R toward the proximal side in the present embodiment. Accordingly, when the end effector 5 is not bent relative to the shaft 3, neither of the interlocking members 51A and 51B engages (comes into contact) with the engaging protrusion 52. FIGS. 3 to 5 show the state where the end effector 5 is not bent relative to the shaft 3.

By bending the end effector 5 relative to the shaft 3, each of the interlocking members 51A and 51B moves together with a corresponding one of the wires 45A and 45B along the predetermined rotation axis R as described above. As a result, the interlocking member 51A or 51B engages with (abuts against) the engaging protrusion 52. For example, when the end effector 5 is bent to one side (the arrow B1 side) of the bending direction relative to the shaft 3 (the predetermined rotation axis R), the interlocking member 51B moves toward the distal side from the state where the end effector 5 is not bent. As a result, the interlocking member 51B engages with the engaging protrusion 52 (the broken line in FIG. 4). At this time, the interlocking member 51A moves further toward the proximal side from the state where the end effector 5 is not bent, and the interlocking member 51A does not engage with the engaging protrusion 52. In contrast, when the end effector 5 is bent to the other side (the arrow B2 side) of the bending direction relative to the shaft 3, the interlocking member 51A moves toward the distal side from the state where the end effector 5 is not bent. As a result, the interlocking member 51A engages with the engaging protrusion 52 (the broken line in FIG. 5). In this case, the interlocking member 51B moves further toward the proximal side from the state where the end effector 5 is not bent, and the interlocking member 51B does not engage with the engaging protrusion 52.

The engagement of the interlocking member 51A with the engaging protrusion 52 generates sliding resistance (a frictional force) between the interlocking member 51A and the engaging protrusion 52. In this embodiment, the interlocking member 51A is fixed to the wire 45A, and the wire (the drive member) 45A is rotatable round the predetermined rotation axis R relative to the housing 2 together with the shaft 3, the end effector 5, the rotating member 25, the bending dial (the operation input unit) 23, and the pulley (the operation force transmitter) 42. Accordingly, the rotation of the shaft 3, the end effector 5, and the wires 45A and 45B around the predetermined rotation axis R relative to the housing 2 is prevented by the sliding resistance between the interlocking member 51A and the engaging protrusion 52. Furthermore, the engagement of the interlocking member 51B with the engaging protrusion 52 generates sliding resistance between the interlocking member 51B and the engaging protrusion 52. Also in this case, the rotation of the shaft 3, the end effector 5, and the wires 45A and 45B around the predetermined rotation axis R relative to the housing 2 is prevented, similarly to the case where the interlocking member 51A engages with the engaging protrusion 52.

The prevention of the rotation of the shaft 3, the end effector 5, and the wires 45A and 45B around the predetermined rotation axis R relative to the housing 2 leads to prevention of the rotation of the shaft 3 around the predetermined rotation axis R caused by the force acting on the end effector 5. As described above, in the present embodiment, the interlocking members 51A and 51B and the engaging protrusion 52 form a locking mechanism 50 that prevents the rotation of the shaft 3 around the predetermined rotation axis R caused by the force acting on the end effector 5.

Next, the function and advantageous effects of the treatment instrument 1 of the present embodiment will be described. When treating a treatment target such as biological tissue by using the treatment instrument 1, an operator holds the housing 2 by hand and inserts the end effector 5 into a body cavity such as an abdominal cavity. Then, the operator adjusts the position and posture of the end effector 5 in the body cavity by rotating the rotating member 25 to rotate the shaft 3 and the end effector 5 around the predetermined rotation axis R, or by operating the bending dial 23 to bend the end effector 5 relative to the shaft 3. After adjusting the position and posture of the end effector 5 so that the treatment target is arranged between the gripping pieces 16 and 17, the operator (surgeon) closes the handle 21 relative to the grip 12 to close the space between the gripping pieces 16 and 17. As a result, the treatment target is gripped between the gripping pieces 16 and 17. By inputting operation with the operation button (27A or 27B) while the treatment target is gripped, the treatment instrument 1 is activated in the predetermined activation mode, and treatment energy (such as high-frequency current) is applied to the treatment target gripped as described above, or a staple is pierced into the treatment target gripped as described above.

In the treatment using the treatment instrument 1, a force may act on the end effector 5 while the end effector 5 is bent relative to the shaft 3 (the predetermined rotation axis R). In this case, since a force acts on the end effector 5 at a position away from the central axis of the shaft 3 (the predetermined rotation axis R), the force acting on the end effector 5 may generate a rotation moment about the predetermined rotation axis R (around the central axis of the shaft 3). In the present embodiment, the interlocking member (51A or 51B) engages with the engaging protrusion 52 while the end effector 5 is bent to some extent relative to the shaft 3. Accordingly, sliding resistance is (a frictional force) is generated between the interlocking member (51A or 51B) and the engaging protrusion 52, which leads to prevention of the rotation of the shaft 3, the end effector 5, and the wires 45A and 45B around the predetermined rotation axis R relative to the housing 2. As a result, the rotation of the end effector 5 and the shaft 3 around the predetermined rotation axis R caused by the force acting on the end effector 5 is prevented, even if a rotation moment around the predetermined rotation axis R is generated by the force acting on the end effector 5.

As described above, in the present embodiment, the rotation of the end effector 5 and the shaft 3 around the predetermined rotation axis R is effectively avoided by the locking mechanism 50 formed of the interlocking members 51A and 51B and the engaging protrusion (the receiver) 52, even if a force acts on the end effector 5 while the end effector 5 is bent relative to the shaft 3 and a rotation moment around the predetermined rotation axis R is generated by the force acting on the end effector 5. As a result, the treatment performance, for example, is properly secured during treatment, etc., performed while the end effector 5 is bent relative to the shaft 3 and the treatment target is gripped between the gripping pieces 16 and 17.

Modification of First Embodiment

Figure 6:
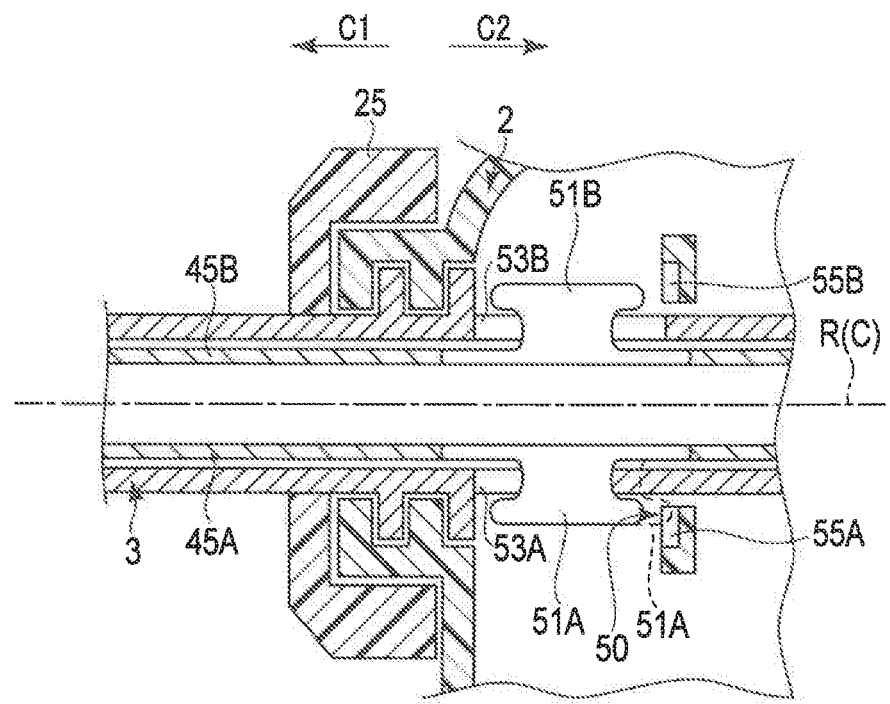
FIG. 6 is a cross-sectional view schematically showing an internal configuration of a housing according to a modification of the first embodiment in a cross section approximately parallel to the predetermined rotation axis.

In a modification of the first embodiment shown in FIG. 6, a pair of slots 53A and 53B, each of which communicates the inside of the shaft 3 and the outside of the shaft 3, are formed on the shaft 3 instead of the slots 47A and 47B. The interlocking member 51A is inserted into the shaft 3 from the slot 53A, and is fixed to the wire (the bending drive member) 45A. Similarly, the interlocking member 51B is inserted into the shaft 3 from the slot 53B, and is fixed to the wire (the bending drive member) 45B. Each of the interlocking members 51A and 51B protrudes from the corresponding one of the slots 53A and 53B to the outside of the shaft 3.

In the present modification, the housing 2 (the housing main body 11) is provided with engaging recesses (the receivers) 55A and 55B. Each of the interlocking members 51A and 51B can engage with a corresponding one of the engaging recesses 55A and 55B inside the housing 2 and outside of the shaft 3. However, when the end effector 5 is not bent relative to the shaft 3 (the predetermined rotation axis R) (a neutral state), the interlocking members 51A and 51B are located away from the engaging recesses 55A and 55B in the direction along the predetermined rotation axis R, and each of the interlocking members 51A and 51B does not engage with the corresponding one of the engaging recesses 55A and 55B.

Also in the present modification, by bending the end effector 5 relative to the shaft 3, each of the interlocking members 51A and 51B moves together with a corresponding one of the wires 45A and 45B along the predetermined rotation axis R as described above. As a result, the interlocking member 51A engages with the engaging recess 55A, or the interlocking member 51B engages with the engaging recess 55B. When the end effector 5 is bent to one side of the bending direction (the arrow B1 side) relative to the shaft 3 (the predetermined rotation axis R), the interlocking member 51A moves to the proximal side from the state where the end effector 5 is not bent. As a result, the interlocking member 51A engages with the engaging recess 55A (the broken line in FIG. 6), and a frictional force is generated between the interlocking member 51A and the engaging recess 55A. This restricts the rotation of the interlocking member 51A around the predetermined rotation axis R relative to the housing 2, and the rotation of the shaft 3, the end effector 5, and the wires 45A and 45B around the predetermined rotation axis R relative to the housing 2 is prevented. In contrast, when the end effector 5 is bent to the other side (the arrow B2 side) of the bending direction relative to the shaft 3, the interlocking member 51B moves to the proximal side from the state where the end effector 5 is not bent. As a result, the interlocking member 51B engages with the engaging recess 55B. This restricts the rotation of the interlocking member 51B around the predetermined rotation axis R relative to the housing 2, and the rotation of the shaft 3, the end effector 5 and the wires 45A and 45B around the predetermined rotation axis R relative to the housing 2 is prevented.

As described above, also in the present modification, the rotation of the shaft 3, the end effector 5, and the wires 45A and 45B around the predetermined rotation axis R relative to the housing 2 is prevented, so that the rotation of the shaft 3 around the predetermined rotation axis R caused by the force acting on the end effector 5 is prevented. In the present modification, the interlocking members 51A and 51B and the engaging recesses 55A and 55B form a locking mechanism 50 that prevents the rotation of the shaft 3 around the predetermined rotation axis R caused by the force acting on the end effector 5.

In a certain modification, each of the interlocking members 51A and 51B is provided with a tooth surface (not shown), and the housing 2 is provided with a tooth surface (not shown) engageable with the respective tooth surfaces of the interlocking members 51A and 51B. Also in the present modification, when the end effector 5 is not bent relative to the shaft 3 (the predetermined rotation axis R) (a neutral state), the respective tooth surfaces of the interlocking members 51A and 51B do not engage with the tooth surface of the housing 2. Then, the interlocking members 51A and 51B move in conjunction with the bending movement of the end effector 5 relative to the shaft 3, so that the tooth surface of the interlocking member (51A or 51B) engages with the tooth surface of the housing 2. The engagement of the tooth surface of the interlocking member (51A or 51B) with the tooth surface of the housing 2 restricts the rotation of the interlocking member (51A or 51B) around the predetermined rotation axis R relative to the housing 2, which leads to prevention of the rotation of the shaft 3, the end effector 5, and the wires 45A and 45B around the predetermined rotation axis R relative to the housing 2. Accordingly, in the present modification, the tooth surfaces of the interlocking members 51A and 51B and the tooth surface of the housing 2 form the locking mechanism 50 that prevents the rotation of the shaft 3 around the predetermined rotation axis R caused by the force acting on the end effector 5.

In the first embodiment and the modification thereof, the interlocking member (51A; 51B) moves together with the drive member (45A; 45B) along a predetermined rotation axis (R) in conjunction with bending movement of the end effector (5) relative to a shaft (3). The receiver (52; 55A; 55B) with which the interlocking member (51A; 51B) can engage is provided in such a manner that rotation of the receiver (52; 55A; 55B) relative to the housing (2) is restricted. When the end effector (5) is bent relative to the shaft (3), the interlocking member (51A; 51B) engages with the receiver (52; 55A; 55B) inside the housing (2). As a result, rotation of the shaft (3) and the drive member (45A; 45B) around the predetermined rotation axis (R) relative to the housing (2) is prevented, and rotation of the shaft (3) around the predetermined rotation axis (R) caused by the force acting on the end effector (5) is prevented.

Second Embodiment

Next, a second embodiment of the present invention will be described with reference to FIGS. 7A to 8 in the second embodiment, the configuration of the first embodiment is modified as indicated below. The same elements as in the first embodiment are denoted by the same reference numerals, and the description of such elements is omitted.

Figure 7A:
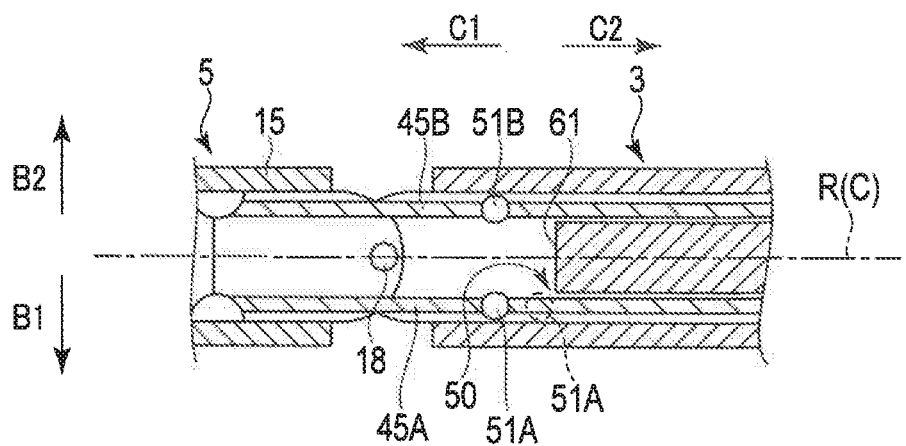
FIG. 7A is a cross-sectional view schematically showing an internal configuration of a shaft according to an example of a second embodiment.
Figure 7B:
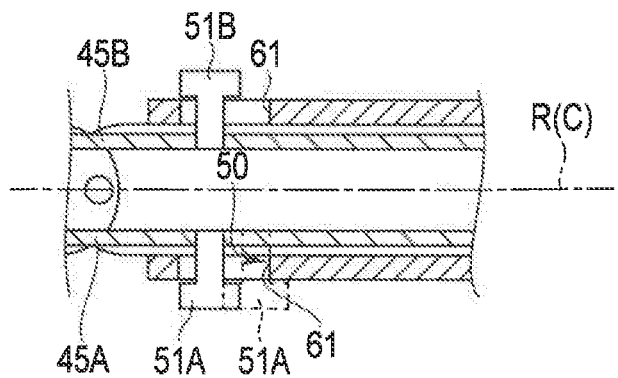
FIG. 7B is a cross-sectional view schematically showing an internal configuration of a shaft according to another example of the second embodiment.
Figure 8:
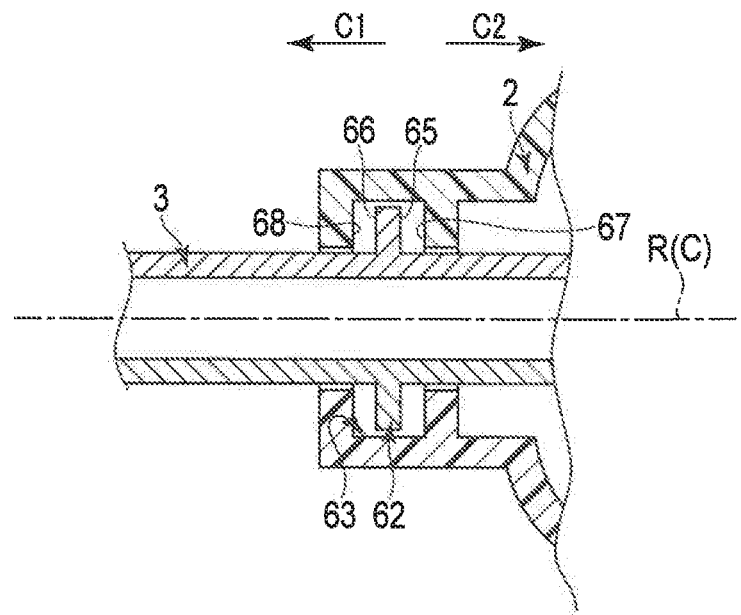
FIG. 8 is a cross-sectional view schematically showing a configuration of a part where the shaft and a housing are coupled according to the second embodiment.

FIGS. 7A and 7B are diagrams showing the internal configuration of the shaft 3, and FIG. 8 is a diagram showing a configuration of a part where the shaft 3 and the housing 2 are coupled. As shown in FIGS. 7A and 7B, also in the present embodiment, the interlocking member 51A is fixed to the wire (the bending drive member) 45A, and the interlocking member 51B is fixed to the wire (the bending drive member) 45B. Accordingly, also in the present embodiment, each of the interlocking members 51A and 51B moves together with a corresponding one of the wires 45A and 45B along the predetermined rotation axis R in conjunction with the bending movement of the end effector relative to the shaft 3.

However, in the present embodiment, the interlocking members 51A and 51B are located inside the shaft 3. In the present embodiment, the shaft 3 is provided with the receiving surface (the receiver) 61 with which the interlocking members 51A and 51B can engage (abut). The receiving surface (the receiver) 61 is provided in such a manner that the rotation of the receiving surface 61 about the predetermined rotation axis R relative to the shaft 3 is restricted. The receiving surface (the receiver) 61 may be integrally formed with the shaft 3, or may be formed as a separate member from the shaft 3. The receiving surface (the receiver) 61 may be fixed to the shaft 3 inside the shaft 3 as shown in FIG. 7A. Alternatively, groove may be formed along the rotation axis R on the outer peripheral wall of the shaft 3 as shown in FIG. 7B, and receiving surface 61 may be provided on the surface by which the groove is formed if the receiving surface (the receiver) 61 is formed in the groove, the interlocking members 51A and 51B engage with the groove and move along the groove so that the interlocking members 51A and 51B can abut against the receiving surface (the receiver) 61. When the end effector 5 is not bent relative to the shaft 3 (the predetermined rotation axis R) (a neutral state), the interlocking members 51A and 51B are located away from the receiving surface 61 in the direction along the predetermined rotation axis R toward the distal side in the present embodiment. Therefore, when the end effector 5 is not bent relative to the shaft 3, neither of the interlocking members 51A and 51B engages (comes into contact) with the receiving surface 61.

By bending the end effector 5 relative to the shaft 3, as described above, each of the interlocking members 51A and 51B moves together with the corresponding one of the wires 45A and 45B along the predetermined rotation axis R. Thus, the interlocking member 51A or 51B engages with (abuts against) the receiving surface 61. For example, when the end effector 5 is bent to one side of the bending direction (the arrow B1 side) relative to the shaft 3 (the predetermined rotation axis R), the interlocking member 51A moves to the proximal side from the state where the end effector 5 is not bent. As a result, the interlocking member 51A engages with the receiving surface 61 (the broken lines in FIGS. 7A and 7B). On the other hand, when the end effector 5 is bent to the other side (the arrow B2 side) of the bending direction relative to the shaft 3, the interlocking member 51B moves to the proximal side from the state where the end effector 5 is not bent. As a result, the interlocking member 51B engages with the receiving surface 61. The engagement (abutment) of the interlocking member (51A or 51B) with the receiving surface (the receiver) 61 leads to a pressing force toward the proximal side acting on the shaft 3 from the interlocking member (51A or 51B).

As shown in FIG. 8, in the present embodiment, the shaft 3 is provided with an engaging protrusion 62 protruding toward the outer peripheral side, and the housing 2 is provided with an engaging recess 63 recessed toward the outer peripheral side. Each of the engaging protrusion 62 and the engaging recess 63 extends over the entire circumference around the predetermined rotation axis R. The engaging protrusion 62 engages with the engaging recess 63, so that the shaft 3 is coupled to the housing 2. The engaging protrusion 62 is movable around the predetermined rotation axis R in the engaging recess 63. Therefore, also in the present embodiment, the end effector 5 and the shaft 3 are rotatable about the predetermined rotation axis R.

The engaging protrusion 62 has a protruding opposed surface (a first abutting surface) 65 facing the proximal side, and a protruding opposed surface 66 facing the distal side. The engaging recess 63 has a recessed opposed surface (a second abutting surface) 67 facing the distal side and a recessed opposed surface 68 facing the proximal side. The protruding opposed surface 65 is opposed to the recessed opposed surface 67, and the protruding opposed surface 66 is opposed to the recessed opposed surface 68. The engaging protrusion 62 is movable (finely movable) along the predetermined rotation axis R (the longitudinal axis C) in the engaging recess 63. Accordingly, the shaft 3 is movable (finely movable) relative to the housing 2. However, the range of movement of the shaft 3 relative to the housing 2 is minute. The protruding opposed surface (the first abutting surface) 65 of the engaging protrusion 62 abuts against the recessed opposed surface (the second abutting surface) 67 of the engaging recess 63, so that the movement of the shaft 3 toward the proximal side relative to the housing 2 is restricted. The protruding opposed surface 66 of the engaging protrusion 62 abuts against the recessed opposed surface 68 of the engaging recess 63, so that the movement of the shaft 3 toward the distal side relative to the housing 2 is restricted.

Because of the configuration as described above, if the interlocking member (51A or 51B) engages with the receiving surface (the receiver) 61 and a pressing force toward the proximal side acts on the shaft 3 from the interlocking member (51A or 51B), the shaft 3 moves toward the proximal side relative to the housing 2 along the predetermined rotation axis R. In correspondence with the movement of the shaft 3 toward the proximal side relative to the housing 2, the protruding opposed surface (the first abutting surface) 65 of the engaging protrusion 62 abuts against the recessed opposed surface (the second abutting surface) 67 of the engaging recess 63. Therefore, when the end effector 5 is bent relative to the shaft 3, sliding resistance (a frictional force) is generated between the protruding opposed surface 65 and the opposed facing surface 67. By the sliding resistance between the protruding opposed surface 65 and the recessed opposed surface 67, rotation of the shaft 3, the end effector 5, and the wires (the bending drive members) 45A and 45B around the predetermined rotation axis R relative to the housing 2 is prevented.

The prevention of the rotation of the shaft 3, the end effector 5, and the wires 45A and 45B around the predetermined rotation axis R relative to the housing 2 leads to prevention of the rotation of the shaft 3 around the predetermined rotation axis R caused by the force acting on the end effector 5 also in the present embodiment. As described above, in the present embodiment, the interlocking members 51A and 51B and the receiving surface 61 form the locking mechanism 50 that prevents the rotation of the shaft 3 around the predetermined rotation axis R caused by the force acting on the end effector 5. As described above, also in the present embodiment, the rotation of the end effector 5 and the shaft 3 around the predetermined rotation axis R is effectively prevented by the locking mechanism 50 formed of the interlocking members 51A and 51B and the receiving surface (the receiver) 61, even if a force acts on the end effector 5 while the end effector 5 is bent relative to the shaft 3 and a rotation moment around the predetermined rotation axis R is generated by the force acting on the end effector 5. Therefore, the present embodiment provides the same function and advantageous effects as those of the first embodiment.

Modification of Second Embodiment

In the second embodiment, the interlocking member (51A or 51B) moves from a state where the end effector 5 is not bent relative to the shaft 3 (the predetermined rotation axis R) (a neutral state) to the proximal side, so that the interlocking member (51A or 51B) engages with the receiving surface (the receiver) 61. However, the configuration is not limited thereto. For example, in a certain modification of the second embodiment shown in FIGS. 9A and 9B, the interlocking member (51A or 51B) moves to the distal side from the state where the end effector 5 is not bent relative to the shaft 3 (a neutral state), so that the interlocking member (51A or 51B) engages with (abuts against) the receiving surface (the receiver) 61 fixed to the shaft 3. For example, when the end effector 5 is bent to one side (the arrow B1 side) of the bending direction relative to the shaft 3, the interlocking member 51B moves toward the distal side from the state where the end effector 5 is not bent. As a result, the interlocking member 51B engages with the receiving surface 61 (the broken lines in FIGS. 9A and 9B). On the other hand, when the end effector 5 is bent to the other side (the arrow B2 side) of the bending direction relative to the shaft 3, the interlocking member 51A moves toward the distal side from a state where the end effector 5 is not bent. As a result, the interlocking member 51A engages with the receiving surface 61. In the present modification, the engagement (abutment) of the interlocking member (51A or 51B) with the receiving surface (the receiver) 61 leads to a pressing force toward the distal side acting on the shaft 3 from the interlocking member (51A or 51B).

Because of the configuration described above, in the present modification, if the interlocking member (51A or 51B) engages with the receiving surface (the receiver) 61 and a pressing force toward the distal side acts on the shaft 3 from the interlocking member (51A or 51B), the shaft 3 moves toward the distal side relative to the housing 2 along the predetermined rotation axis R. In correspondence with the movement of the shaft 3 toward the distal side relative to the housing 2, the protruding opposed surface (the first abutting surface) 66 of the engaging protrusion 62 abuts against the recessed opposed surface (the second abutting surface) 68 of the engaging recess 63. Therefore, when the end effector 5 is bent relative to the shaft 3, sliding resistance (a frictional force) is generated between the protruding opposed surface 66 and the recessed opposed surface 68. By the sliding resistance between the protruding opposed surface 66 and the recessed opposed surface 68, rotation of the shaft 3, the end effector 5, and the wires (the bending drive members) 45A and 45B around the predetermined rotation axis R relative to the housing 2 is prevented. Therefore, also in the present modification, the rotation of the shaft 3 about the predetermined rotation axis R caused by the force acting on the end effector 5 is prevented. As described above, also in the present modification, the interlocking members 51A and 51B and the receiving surface 61 form the locking mechanism 50 that prevents the rotation of the shaft 3 around the predetermined rotation axis R caused by the force acting on the end effector 5.

In the second embodiment and the modification thereof, the interlocking member (51A; 51B) moves together with the drive member (45A; 45B) along the predetermined rotation axis (R) in conjunction with the bending movement of the end effector (5) relative to the shaft (3). The receiver (61) with which the interlocking member (51A; 51B) can engage is provided in such a manner that the rotation of the receiver (61) relative to the shaft (3) is restricted. When the end effector (5) is bent relative to the shaft (3), the interlocking member (51A; 51B) engages with the receiver (61). As a result, the shaft (3) moves along the predetermined rotation axis (R) relative to the housing (2). In correspondence with the movement of the shaft (3) relative to the housing (2), the first abutting surface (65; 66) of the shaft (3) abuts against the second abutting surface (67; 58) of the housing (2). As a result, the rotation of the shaft (3) and the drive member (45A; 45B) around the predetermined rotation axis (R) relative to the housing (2) is prevented, and the rotation of the shaft (3) around the predetermined rotation axis (R) caused by the force acting on the end effector (5) is prevented.

Modifications of First Embodiment and Second Embodiment

In the first and second embodiments and the modifications thereof, the drive member (45A; 45B) moves along the predetermined rotation axis (R), so that the end effector (5) is bent relative to the shaft (3), and the drive member (45A; 45B) is rotatable together with the shaft (3) around the predetermined rotation axis (R). Then, in conjunction with the bending movement of the end effector (5) relative to the shaft (3), the interlocking member (51A; 51B) moves together with the drive member (45A; 45B) along the predetermined rotation axis (R), When the end effector (5) is bent relative to the shaft (3), the interlocking member (51A; 51B) engages with the receiver (52; 55A; 55B; 61), the receiver (52; 55A; 55B; 61) being provided in such a manner that the rotation of the receiver relative to the housing (2) is restricted or that the rotation of receiver relative to the shaft (3) is restricted. As a result, the rotation of the shaft (3) and the drive member (45A; 45B) around the predetermined rotation axis (R) relative to the housing (2) is prevented, and the rotation of the shaft (3) around the predetermined rotation axis (R) caused by the force acting on the end effector (5) is prevented.

Third Embodiment

Next, a third embodiment of the present invention will be described with reference to FIGS. 10 and 11. In the third embodiment, the configuration of the first embodiment is modified as indicated below. The same elements as in the first embodiment are denoted by the same reference numerals, and the description of such elements is omitted.

Figure 10:
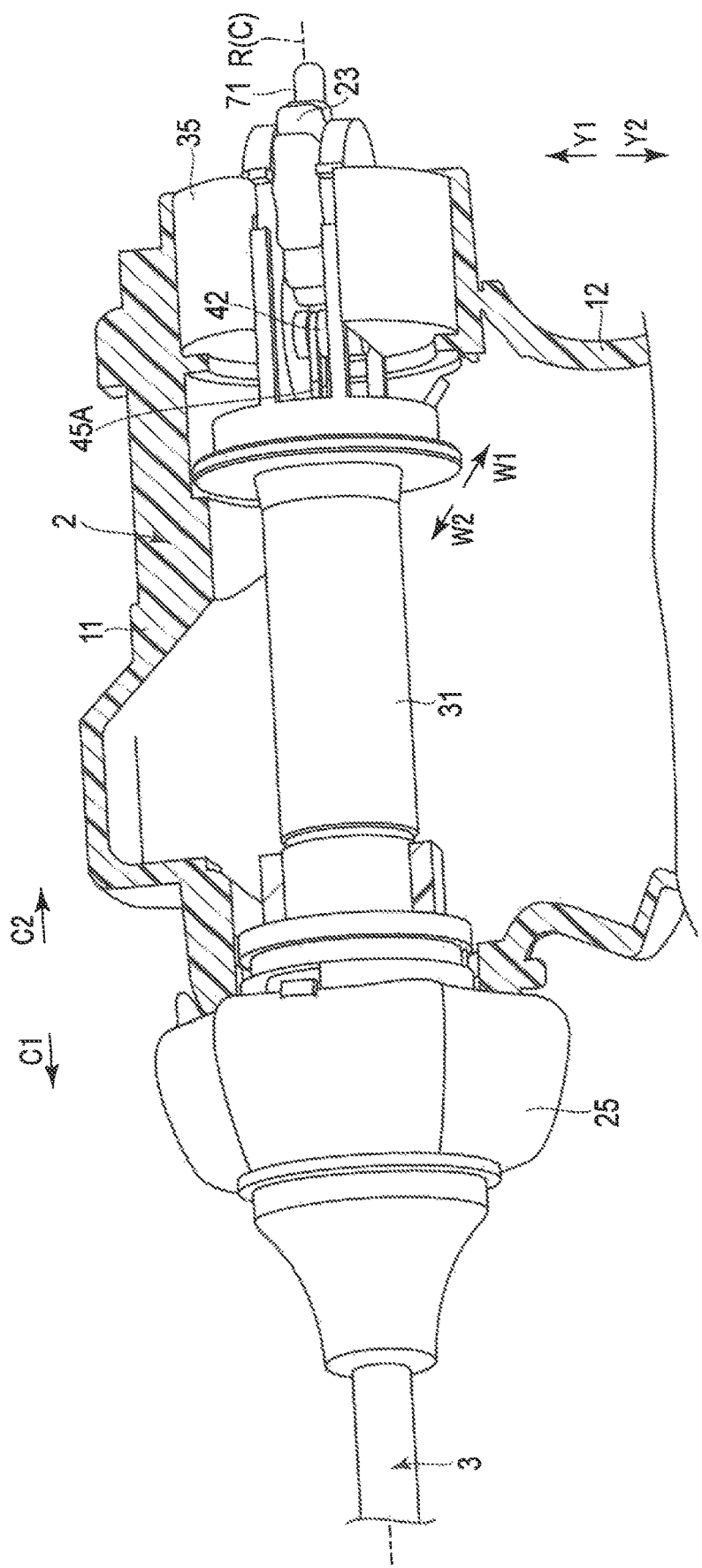
FIG. 10 is a perspective view schematically showing an internal configuration of a housing according to the third embodiment.
Figure 11:
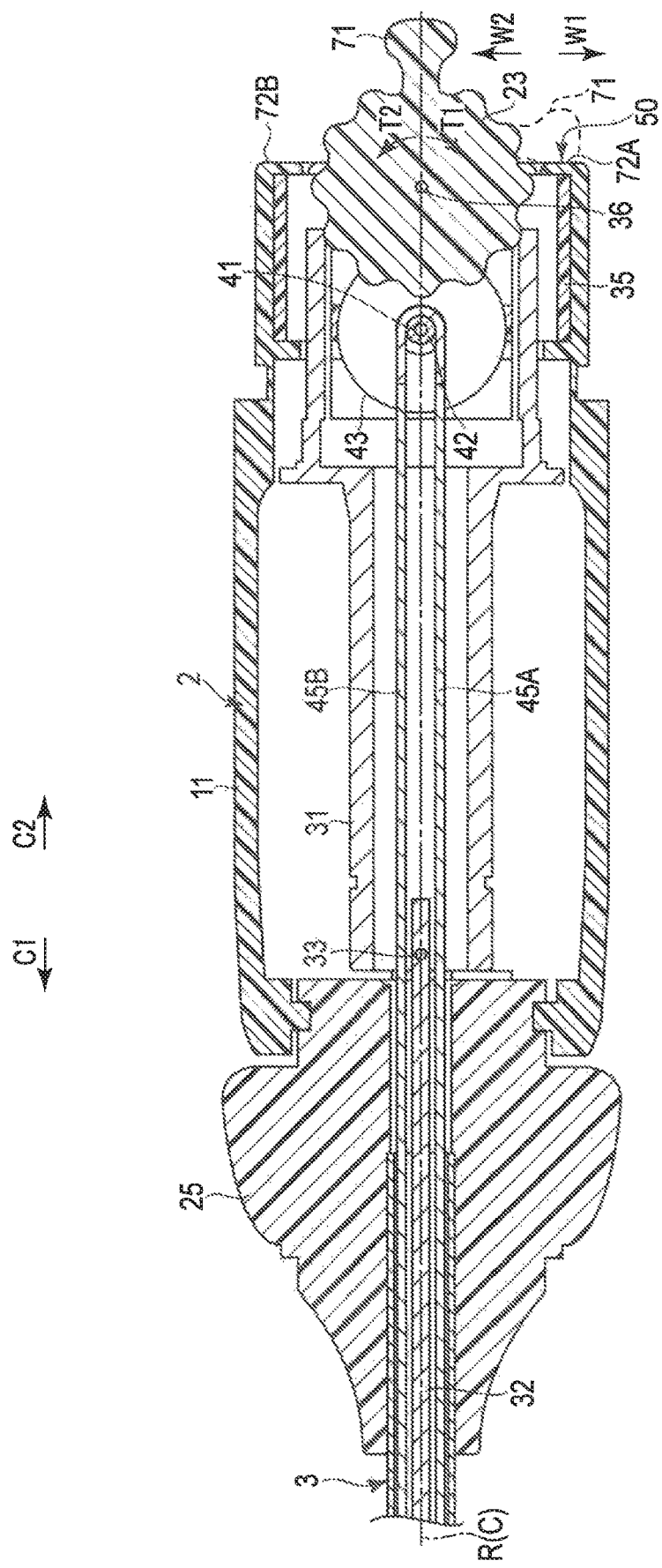
FIG. 11 is a cross-sectional view schematically showing the internal configuration of the housing according to the third embodiment in a cross section approximately parallel to a predetermined rotation axis and approximately parallel to a width direction of the housing.

FIGS. 10 and 11 are diagrams showing configurations of the inside the housing main body 11 of the housing 2 and the inside the rotating member (the rotating knob) 25. FIG. 10 is a perspective view, and FIG. 11 is a cross-sectional view which is approximately parallel to the predetermined rotation axis R (the longitudinal axis C) and approximately parallel to the width direction (the direction indicated by arrow W1 and arrow W2) of the housing 2. As shown in FIGS. 10 and 11, in the present embodiment, the interlocking member 71 that moves in conjunction with the bending movement of the end effector 5 relative to the shaft 3 is provided on the bending dial 23 that is a bending operation input section. In the present embodiment, the interlocking member 71 protrudes to the proximal side in the bending dial 23, and is exposed to the outside of the housing 2. The interlocking member 71 is fixed to the bending dial 23, and is rotationally movable together with the bending dial 23 around the supporting shaft 36 relative to the base member 35. Since the interlocking member 71 is provided in the bending dial 23, also in the present embodiment, the interlocking member 71 is provided independently of (separately from) the shaft 3.

In the present embodiment, the operation of bending the end effector 5 relative to the shaft 3 is input at the bending dial 23, so that the bending dial 23 and the interlocking member 71 rotationally move together around the supporting shaft 36. Therefore, the interlocking member 71 moves in conjunction with the bending movement of the end effector 5 relative to the shaft 3, and moves in conjunction with the operation input at the bending dial 23 and in conjunction with the activation of the pulley (the operation force transmitter) 42 based on the operation input at the bending dial (the operation inputter) 23.

Also in the present embodiment, the base member 35 and the bending dial 23 are installed in a part of the outer surface of the housing main body 11 facing the proximal side. At the part of the outer surface of the housing main body 11 facing the proximal side, receiving surfaces (the receivers) 72A and 72B with which the interlocking member 71 can engage (abut) provided. In other words, in the present embodiment, the receiving surfaces 72A and 72B are provided in such a manner that the rotation of the receiving surfaces 72A and 72B around the predetermined rotation axis R relative to the housing 2 is restricted. The receiving surfaces 72A and 72B may be integrally formed with the housing 2, or may be formed as separate members from the housing 2. Also in the present embodiment, when the operation force at the rotating member 25 is applied to rotate the shaft 3 around the predetermined rotation axis a rotation drive force around the predetermined rotation axis R is transmitted from the shaft 3 to the bending dial (the bending operation input member) 23 and the pulley (the operation force transmitter) 42 via the movable member 31 and the base member 35. As a result, also in the present embodiment, the bending dial 23, the pulley 42, and the wires (the bending drive members) 45A and 45B rotate together with the shaft 3 (the rotating member) and the end effector 5 around the predetermined rotation axis R relative to the housing 2.

When the end effector 5 is not bent relative to the shaft 3 (the predetermined rotation axis R) (a neutral state), the interlocking member 71 is located away from the receiving surfaces 72 A and 72 B, and the interlocking member 71 does not engage (contact) with any of the receiving surfaces 72A and 72B. FIGS. 10 and 11 show state where the end effector 5 is not bent relative to the shaft 3. When the bending dial 23 is rotationally moved around the supporting shaft 36 by the operation input so as to bend the end effector 5 relative to the shaft 3, the interlocking member 71 moves in conjunction with the bending. As a result, the interlocking member 71 rotationally moves together with the bending dial 23 around the supporting shaft 36, and the interlocking member 71 engages with (abuts against) the receiving surface (72A or 72B).

For example, when the bending dial 23 rotations y moves to one side (the arrow T1 side) of the circumferential direction of the supporting shaft 36, and the end effector 5 is bent to one side (the arrow B1 side) of the bending direction relative to the shaft 3 (the predetermined rotation axis R), the interlocking member 71 rotationally moves to one side (the arrow T1 side) of the circumferential direction of the supporting shaft 36 from the state where the end effector 5 is not bent. As a result, the interlocking member 71 engages with the receiving surface (the receiver) 72A (the broken line in FIG. 11). In contrast, when the bending dial 23 rotationally moves to the other side (the arrow T2 side) of the circumferential direction of the supporting shaft 36, and the end effector 5 is bent relative to the shaft 3 (the predetermined rotation axis R) to one side (the arrow B2 side) of the bending direction, the interlocking member 71 rotationally moves to the other side (the arrow T2 side) of the circumferential direction of the supporting shaft 36 from the state where the end effector 5 is not bent. As a result, the interlocking member 71 engages with (abuts against) the receiving surface 72B.

The engagement of the interlocking member 71 with the receiving surface (72A or 72B) generates sliding resistance (a frictional force) between the interlocking member 71 and the receiving surface (72A or 72B). Herein, in the present embodiment, the interlocking member 71 is fixed to the bending dial (the operation input section) 23. Accordingly, the sliding resistance between the interlocking member 71 and the receiving surface (72A or 72B) prevents rotation of the bending dial (the operation input member) 23 and the pulley (operation force transmitter) 42 around the predetermined rotation axis R relative to the housing 2. As described above, in the present embodiment, the bending dial 23 and the pulley 42 are rotatable together with the shaft 3, the end effector 5, and the rotating member 25 about the predetermined rotation axis R relative to the housing 2. Accordingly, the prevention of the rotation of the bending dial (the operation input section) 23 and the pulley (the operation force transmitter) 42 around the predetermined rotation axis R relative to the housing 2 leads to prevention of the rotation of the shaft 3, the end effector 5, and the wires 45A and 45B around the predetermined rotation axis R relative to the housing 2.

As described above, also in the present embodiment, the rotation of the shaft 3, the end effector 5, and the wires 45A and 45B about the predetermined rotation axis R with respect to the housing 2 is prevented, so that the rotation of the shaft 3 around the predetermined rotation axis R caused by the force acting on the end effector 5 is prevented. As described above, in the present embodiment, the interlocking member 71 and the receiving surfaces (the receivers) 72A and 72B form the locking mechanism 50 that prevents the rotation of the shaft 3 around the predetermined rotation axis R caused by the force acting on the end effector 5.

As described above, in the present embodiment, the rotation of the end effector 5 and the shaft 3 around the predetermined rotation axis R is effectively prevented by the locking mechanism 50 formed of the interlocking member 71 and the receiving surfaces (the receivers) 72A and 72B, even if a force acts on the end effector 5 while the end effector 5 is bent with respect to the shaft 3 and a rotation moment around the predetermined rotation axis R is generated by the force acting on the end effector 5. Therefore, the present embodiment provides the same function and advantageous effects as those of the first embodiment.

Modification of Third Embodiment

In the third embodiment, the interlocking member 71 is fixed to the bending dial 23 as the bending operation input section. However, the configuration is not limited thereto. For example, in a modification (not shown) of the third embodiment, the interlocking member (71) is fixed to a member forming the operation force transmitter such as the pulley (42). Also in the present modification, the interlocking member (71) moves in conjunction with the bending movement of the end effector (5) relative to the shaft (3), and moves in conjunction with the operation input at the operation input section, such as the bending dial 23, and in conjunction with the activation of the operation force transmitter, such as the pulley (42), based on the operation at the operation input section. Then, when the end effector (5) is bent relative to the shaft (3), the interlocking member (71) engages with a receiver (not shown) provided on the housing (2). The engagement of the interlocking member (71) with the receiver prevents the rotation of the operation input unit (23) and the operation force transmitter (42) around the predetermined rotation axis (R) relative to the housing (2). Also in the present modification, the operation input member (23) and the operation force transmitter (42) are rotatable together with the shaft (3) and the end effector (5) around a predetermined rotation axis R relative to the housing (2). Accordingly, also in the present modification, the rotation of the shaft (3), the end effector (5), and the bending drive members (45A, 45B) around the predetermined rotation axis (R) relative to the housing (2) is prevented.

In the third embodiment and the modification thereof, the rotation of the shaft (3) around the predetermined rotation axis (R) transmits a rotation drive force from the shaft (3) to the operation input member (23) and the operation force transmitter (42), which causes the operation input member (23) and the operation force transmitter (42) to rotate together with the shaft (3) around the predetermined rotation axis (R). Furthermore, the interlocking member (71) moves in conjunction with the bending movement of the end effector (5) relative to the shaft (3), and moves in conjunction with the operation input at the operation input member (23) and in conjunction with the activation of the operation force transmitter (42) based on the operation input. When the end effector (5) is bent relative to the shaft (3), the interlocking member (71) engages with the receiver (72A; 72B) provided in such a manner that the rotation of receiver relative to the housing (2) is restricted, and the rotation of the operation input member (23) and the operation force transmitter (42) around the predetermined rotation axis (R) relative to the housing (2) is prevented. As a result, the rotation of the shaft (3) and the drive member (45A; 45B) around the predetermined rotation axis (R) relative to the housing (2) is prevented, and the rotation of the shaft (3) around the predetermined rotation axis (R) caused by the force acting on the end effector (5) is prevented.

Fourth Embodiment

Next, a fourth embodiment of the present invention will be described with reference to FIG. 12. In the fourth embodiment, the configuration of the first embodiment is modified as described below. The same elements as in the first embodiment are denoted by the same reference numerals, and the description of such elements is omitted.

Figure 12:
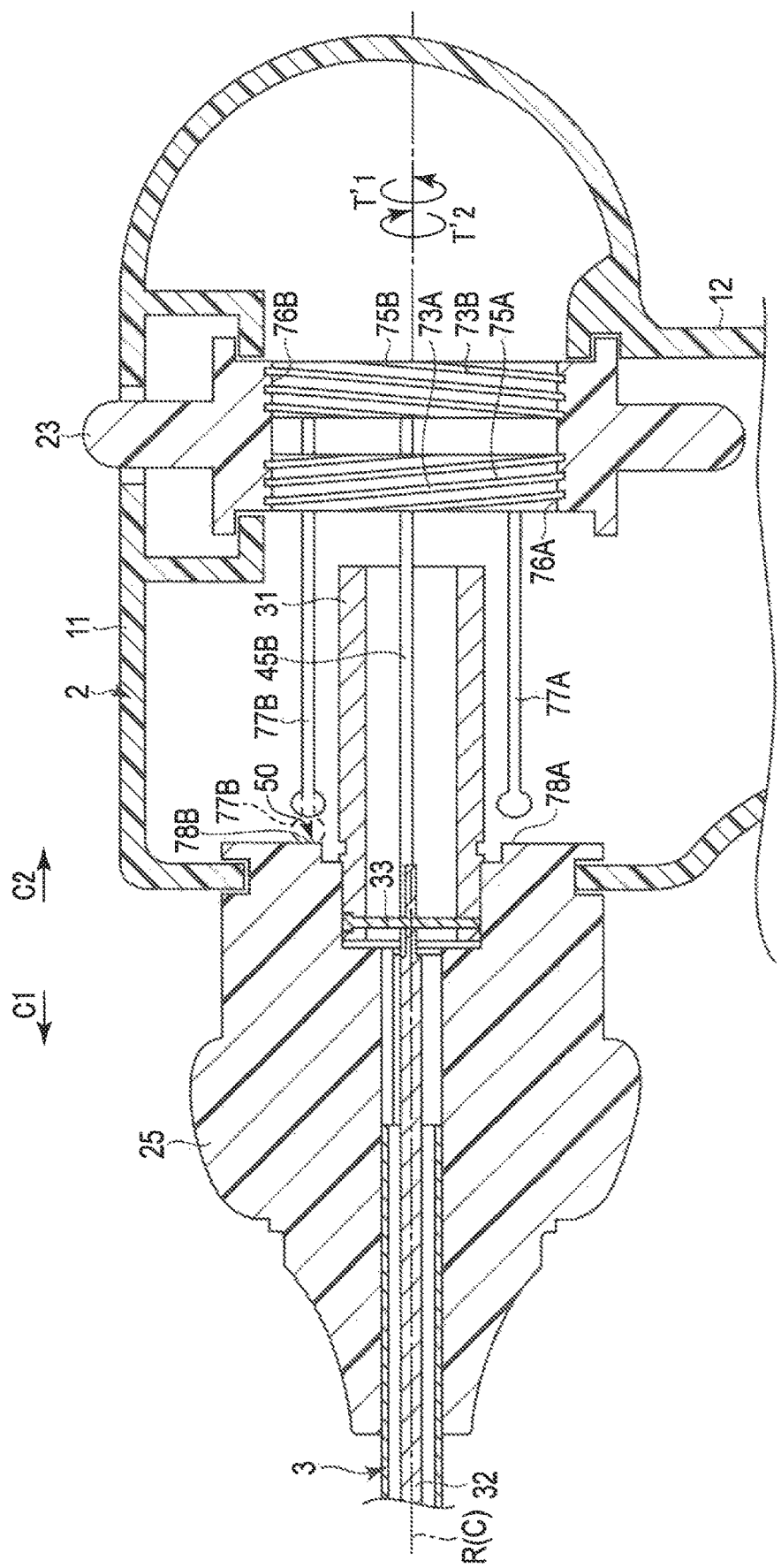
FIG. 12 is a cross-sectional view schematically showing an internal configuration of a housing according to a fourth embodiment in a cross section approximately perpendicular to a width direction of the housing.

FIG. 12 is a diagram showing an internal configuration of the housing main body 11 of the housing 2, and an internal configuration of the rotating member (the rotating knob) 25. FIG. 12 shows a cross section approximately perpendicular to the width direction of the housing 2. As shown in FIG. 12, in the present embodiment, even if the shaft 3 is rotated around the predetermined rotation axis R, the rotation drive force is not transmitted from the shaft 3 to the bending dial (the bending operation input section) 23, and the bending dial 23 does not rotate together with the shaft 3. However, also in the present embodiment, the shaft 3 including the rotating member 25 can rotate together with the end effector 5 about the predetermined rotation axis R relative to the housing 2.

In the present embodiment, the bending dial 23 is exposed to the outside of the housing 2 at a position of the outer surface of the housing main body 11 facing the opposite side of the side on which the grip 12 is located relative to the predetermined rotation axis R (the longitudinal axis C). In the present embodiment, the bending dial 23 is rotationally movable around the central axis of the bending dial 23 relative to the housing 2, independently of the shaft 3 and the rotating member 25. The central axis of the bending dial 23 is approximately parallel to the predetermined rotation axis R (the longitudinal axis C). The central axis of the bending dial 23 may be provided coaxially with the predetermined rotation axis R.

Inside the housing main body 11, moving bodies 73A and 73B are attached to the bending dial 23. Each of the moving bodies 73A and 73B is arranged approximately coaxially with the bending dial 23. In this embodiment, the moving body 73A is located on the distal side relative to the moving body 73B. A male screw 75A is formed on the outer peripheral surface of the moving body 73A, and a male screw 75B is formed on the outer peripheral surface of the moving body 73B. Also, on the inner peripheral surface of the bending dial 23, a female screw 76A screwable to the male screw 75A and a female screw 76B screwable to the male screw 75B are formed. By the male screw 75A being screwed to the female screw 76A, the moving body 73A is attached to the bending dial 23, and by the male screw 75B being screwed to the female screw 76B, the moving body 73B is attached to the bending dial 23. The spiral of the male screw 75A and the spiral of the male screw 75B are reverse-winding relative to each other; for example, the male screw 75A is a right screw and the male screw 75B is a left screw. Furthermore, in the present embodiment, one end (the proximal end) of the wire (the bending drive member) 45A is connected to the moving body 73A, and one end of the wire (the bending drive member) 45B is connected to the moving body 73B.

The bending dial 23 rotationally moves based on the operation input at the bending dial 23, so that the moving bodies 73A and 73B are activated, and the moving bodies 73A and 73B move along the predetermined rotation axis R (the central axis of the bending dial 23). As a result, the moving bodies 73A and 73B as the operation force transmitters transmit an operation force for bending the end effector 5 relative to the shaft 3. At this time the male screws 75A and 75B are reverse-winding relative to each other, the moving bodies 73A and 73B move toward the opposite side from each other along the predetermined rotation axis R. The movement of the moving bodies 73A and 73B as operation force transmitters transmits the operation force for bending the end effector 5 from each of the moving bodies 73A and 73B to a corresponding one of the wires 45A and 45B. As a result, the wires 45A and 45B move along the predetermined rotation axis R (the longitudinal axis C) relative to the shaft 3 and the movable member 31. The movement of the wires 45A and 45B causes the end effector 5 to bend relative to the shaft 3 (predetermined rotation axis R).

In this embodiment, when the bending dial 23 rotationally moves to one side (the arrow T'1 side) around the central axis of the bending dial 23, the moving body 73A moves toward the proximal side, and the moving body 73B moves toward the distal side. As a result, the wire 45A moves toward the proximal side (i.e., the wire 45A is pulled), and the wire 45B moves toward the distal side (i.e., the wire 45B is relaxed). As a result, the end effector 5 is bent to one side (the arrow B1 side) of the bending direction relative to the shaft 3 (the predetermined rotation axis R). In contrast, when the bending dial 23 rotationally moves to the other side (the arrow T'2 side) around the central axis of the bending dial 23, the moving body 73B moves toward the proximal side, and the moving body 73A moves to the distal side. As a result, the wire 45B moves toward the proximal side, and the wire 45A moves toward the distal side. Accordingly, the end effector 5 is bent to the other side (the arrow B2 side) of the bending direction relative to the shaft 3.

Also in this embodiment, the wires (the bending drive members) 45A and 45B are rotatable together with the shaft 3 (the rotating member 25) and the end effector 5 around the predetermined rotation axis R relative to the housing 2. However, in the present embodiment, even if the shaft 3 rotates about the predetermined rotation axis R, the bending dial (the operation input section) 23 and the moving bodies (the operation force transmitters) 73A and 73B do not rotate together with the shaft 3. Therefore, in the present embodiment, the wires (the bending drive members) 45A and 45B are rotatable together with the end effector 5 and the shaft 3 around the predetermined rotation axis R relative to the bending dial (the operation input member) 23 and the moving bodies (the operation force transmitters) 73A and 73B.

In the present embodiment, an interlocking member 77A is fixed to the moving body 73A, and an interlocking member 77B is fixed to the moving body 73B. The interlocking member (the rod member) 77A extends from the moving body 73A toward the distal side, and the interlocking member (the rod member) 77B extends from the moving body 73B toward the distal side. In the present embodiment, the operation of bending the end effector 5 relative to the shaft 3 is input with the bending dial 23, so that the interlocking member 77A moves together with the moving body 73A along the predetermined rotation axis R, and the interlocking member 77B moves together with the moving body 73B along the predetermined rotation axis R. Accordingly, the interlocking members 77A and 77B move in conjunction with the bending movement of the end effector 5 relative to the shaft 3, and move in conjunction with the operation input at the bending dial (the operation input member) 23 and in conjunction with the activation of the moving bodies (the operation force transmitters) 73A and 73B based on the operation input at the bending dial 23. Since each of the interlocking members 77A and 77B is provided on the corresponding one of the moving bodies 73A and 73B, the interlocking members 77A and 77B are provided independently of (separately from) the shaft 3 also in the present embodiment.

Furthermore, in the present embodiment, a receiving surface (a receiver) 78A with which the interlocking member 77A can engage (abut) and a receiving surface (a receiver) 78B with which the interlocking member 77B can engage (abut) are provided on the rotating member 25, the rotating member 25 being a part of the shaft 3. In other words, the receiving surfaces 78A and 78B are provided in such a manner that the rotation of the receiving surfaces 78A and 78B around the predetermined rotation axis R relative to the shaft 3 is restricted. The receiving surfaces 78A and 78B may be integrally formed with the shaft 3, or may be formed as separate members from the shaft 3. When the end effector 5 is not bent relative to the shaft 3 (the predetermined rotation axis R) (a neutral state), each of the interlocking members 77A and 77B is located away from the corresponding one of the receiving surfaces 78A and 78B, and each of the interlocking members 77A and 77B does not engage (contact) with any of the receiving faces 78A and 78B. FIG. 12 shows a state where the end effector 5 is not bent relative to the shaft 3. When the bending dial 23 is rotationally moved by an operation input so as to bend the end effector 5 relative to the shaft 3, the interlocking members 77A and 77B also move in conjunction with the bending. As a result, each of the interlocking members 77A and 77B moves together with the corresponding one of the moving bodies 73A and 73B along the predetermined rotation axis R, and the interlocking member (77A or 77B) engages with (abut against) the corresponding receiving surface (corresponding one of 78A and 78B).

For example, when the bending dial 23 rotationally moves to one side (the arrow T'1 side) of the circumferential direction of the bending dial 23, and the end effector 5 is bent to one side (the arrow B1 side) of the bending direction relative to the shaft 3 (the predetermined rotation axis R), the interlocking member 77B moves together with the moving body 73B to the distal side (the arrow C1 side) from the state where the end effector 5 is not bent. As a result, the interlocking member 77B engages with the receiving surface (the receiver) 78B (the broken line in FIG. 12). In contrast, when the bending dial 23 rotationally moves to the other side (the arrow T'2 side) of the circumferential direction of the bending dial 23, and the end effector 5 is bent to the other side (the arrow B2 side) of the bending direction relative to the shaft 3, the interlocking member 77A moves together with the moving body 73A toward the distal side from the state where the end effector 5 is not bent. As a result, the interlocking member 77A engages with (abuts against) the receiving surface 78A.

The engagement of the interlocking member (77A or 77B) with the corresponding receiving surface (corresponding one of 78A and 78B) generates sliding resistance (a frictional force) between the interlocking member (77A or 77B) and the receiving surface (corresponding one of 78A and 78B). Therefore, the sliding resistance between the interlocking member (77A or 77B) and the receiving surface (corresponding one of 78A and 78B) prevents the rotation of the end effector 5 and the shaft 3 including the rotating member 25 relative to the bending dial (the operation input member) 23 and the moving bodies (the operation force transmitters) 73A and 73B about the predetermined rotation axis R. At this time, the rotation of the wires (the bending drive members) 45A and 45B around the predetermined rotation axis R relative to the bending dial 23 and the moving bodies 73A and 73B is also prevented.

In the present embodiment, as described above, the prevention of the rotation of the shaft 3, the end effector 5, and the wires 45A and 45B around the predetermined rotation axis R relative to the bending dial (the operation input section) 23 and the moving bodies (the operation force transmitters) 73A and 73B leads to prevention of the rotation of the shaft 3 around the predetermined rotation axis R due to the force acting on the end effector 5. Accordingly, the interlocking members 77A and 77B and the receiving surfaces (the receivers) 78A and 78B form the locking mechanism 50 for preventing the rotation of the shaft 3 around the predetermined rotation axis R caused by the force acting on the end effector 5.

As described above, also in the present embodiment, the rotation of the end effector 5 and the shaft 3 around the predetermined rotation axis R is effectively prevented by the locking mechanism 50 formed of the interlocking members 77A and 77B and the receiving surfaces (the receivers) 78A and 78B, even if a force acts on the end effector 5 while the end effector 5 is bent relative to the shaft 3 and a rotation moment around the predetermined rotation axis R is generated by the force acting on the end effector 5. Therefore, the present embodiment provides the same function and advantageous effects as those of the first embodiment.

Modification of Fourth Embodiment

In the fourth embodiment, each of the interlocking members 77A and 77B fixed to the corresponding one of the moving bodies 73A and 73B, and is provided in the operation force transmitter. However, the configuration is not limited thereto. For example, in a modification (not shown) of the fourth embodiment, an interlocking member (not shown) is attached to the bending dial 23. Also in the present modification, the interlocking member moves in conjunction with the bending movement of the end effector (5) relative to the shaft (3), and moves in conjunction with the operation input at the operation input member such as the bending dial 23 and in conjunction with the activation of the operation force transmitter (73A; 73B) based on the operation input at the operation input member. Then, when the end effector (5) is bent relative to the shaft (3), the interlocking member engages with a receiver (not shown) provided on the shaft (3). Also in the present modification, the engagement of the interlocking member with the receiver prevents the rotation of the shaft (3), the end effector (5), and the bending drive member (45A, 45B) around the predetermined rotation axis (R) relative to the operation input member (23) and the operation force transmitter (73A; 73B).

In the fourth embodiment and the modification thereof, the operation input member (23) and the operation force transmitter (73A; 73B) do not rotate together with the shaft (3), even if the shaft (3) rotates around the predetermined rotation axis (R). The interlocking member (77A; 77B) moves in conjunction with the bending movement of the end effector (5) relative to the shaft (3), and moves in conjunction with the operation input at the operation input member (23) and in conjunction with the activation of the operation force transmitter (73A; 73B) based on the operation input. When the end effector (5) is bent relative to the shaft (3), the interlocking member (77A; 77B) engages with the receiver (78A; 78B), the receiver (78A; 78B) being provided in such a manner that rotation of the receiver (78A; 78B) relative to the shaft (3) is restricted. As a result, the rotation of the shaft (3) and the drive member (45A; 45B) around the predetermined rotation axis (R) relative to the operation input member (23) and the operation force transmitter (73A; 73B) is prevented, and the rotation of the shaft (3) around the predetermined rotation axis (R) caused by the force acting on the end effector (5) is prevented.

Other Modifications

In a configuration where the operation input section (23) and the operation force transmitter (73A; 73B) do not rotate together with the shaft (3) even if the shaft (3) rotates around the predetermined rotation axis (R) as in the fourth embodiment and the modification thereof, the interlocking member (51A; 51B) may be fixed to the drive member (45A; 45B) as in the first and second embodiments and the modifications thereof. Also in this case, similarly to the first and second embodiments and the modifications thereof, the interlocking member (51A; 51B) moves together with the drive member (45A; 45B) along the predetermined rotation axis (R) in conjunction with the bending movement of the end effector (5) relative to the shaft (3). When the end effector (5) is bent relative to the shaft (3), the interlocking member (51A; 51B) engages with a receiver (52; 55A; 55B; 61), the receiver (52; 55A; 55B; 61) being provided in such a manner that the rotation of the receiver (52; 55A; 55B; 61) relative to the housing (2) is restricted or that the rotation of the receiver (52; 55A; 55B; 61) relative to the shaft (3) is restricted. As a result, the rotation of the shaft (3) and the drive member (45A; 45B) around the predetermined rotation axis (R) relative to the housing (2) is prevented, and the rotation of the shaft (3) around the predetermined rotation axis (R) caused by the force acting on the end effector (5) is prevented.

Figure 13:
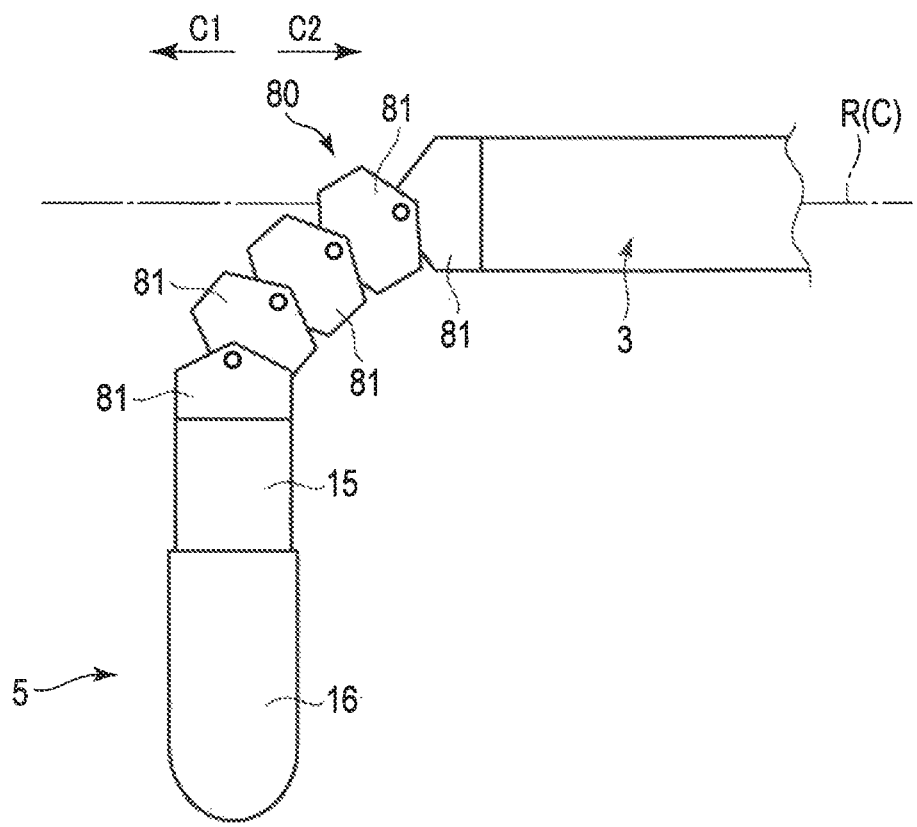
FIG. 13 is a schematic diagram showing a configuration of a distal portion of a treatment instrument according to a modification of the first to fourth embodiments.

The treatment instrument, in which the rotation moment around the predetermined rotation axis R is generated by the force acting on the end effector 5, is not limited to the treatment instrument 1 provided with the bending joint 18 as described in, for example, the above-described embodiment. For example, as in a modification of the first to fourth embodiments shown in FIG. 13, the curving section 80 may be provided on the distal side relative to the shaft 3, instead of the bending joint 18. In the curving section 80, a plurality of curving pieces 81 are juxtaposed, and each of the curving pieces 81 is pivotally coupled to the adjacent curving piece(s) (corresponding one or two of 81). Instead of the bending dial (the bending operation input member) 23, a curving operation input member is provided on the housing 2, and an operation force transmitter (not shown) is activated by operating the curving operation input member, thereby transmitting an operation force to a curving drive member (not shown) such as a wire or a leaf spring. By transmitting the operation force to the curving drive member, the curving drive member is driven to move along the predetermined rotation axis R. As a result, the curving section 80 is activated, and the end effector 5 including the curving section 80 is curved relative to the shaft 3 (the predetermined rotation axis R).

A force acts on the end effector 5 while the end effector 5 is curved relative to the shaft 3, so that a force acts on the position away from the predetermined rotation axis R as described above; accordingly, a rotation moment around the predetermined rotation axis R (around the central axis of the shaft 3) may be generated. Also in this modification, by applying the same configuration as the above-described embodiments, for example, the rotation of the end effector 5 and the shaft 3 around the predetermined rotation axis R is effectively prevented, even if a rotation moment around the predetermined rotation axis R is generated by the force acting on the end effector 5.

In the above-described embodiments, for example, a treatment instrument (1) includes a holdable housing (2), a shaft (3) rotatable around a predetermined rotation axis (R) relative to the housing (2), and an end effector (5) attached to the distal portion of the shaft (3) and bendable or curable relative to the shaft (3). The treatment instrument (1) includes a locking mechanism (50). The locking mechanism (50) includes an interlocking member (51A; 51B; 71; 77A; 77B) provided separately from the shaft (3), and a receiver (52; 55A; 55B; 61; 72A; 72B; 78A; 78B) provided in such a manner that the rotation of the receiver relative to the housing (2) is restricted or the rotation of the receiver relative to the shaft (3) is restricted. The interlocking member (51A; 51B; 71; 77A; 77B) moves in conjunction with the bending movement or the curving movement of the end effector (5) relative to the shaft (3). When the end effector (5) is bent or curved relative to the shaft (3), the rotation of the shaft (3) around the predetermined rotation axis (R) is prevented by engagement of the interlocking member (51A; 51B; 71; 77A; 77B) with the receiver (52; 55A; 55B; 61; 72A; 72B; 78A; 78B).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
   a holdable housing;
   a shaft rotatable around a predetermined rotation axis relative to the housing;
   an end effector attached to a distal portion of the shaft, and bendable relative to the shaft;
   a drive member configured to move along the predetermined rotation axis so as to bend the end effector relative to the shaft, the drive member being rotatable together with the shaft around the predetermined rotation axis; and
   a locking mechanism comprising:
      an interlocking member stationarily fixed to the drive member and being independent of the shaft and configured to move in conjunction with bending movement of the end effector relative to the shaft; and
      a receiver provided in such a manner that rotation of the receiver relative to the housing is restricted or in such a manner that rotation of the receiver relative to the shaft is restricted, the receiver being configured to engage with the interlocking member while the end effector is bent relative to the shaft, thereby preventing rotation of the shaft around the predetermined rotation axis,
   wherein the interlocking member is configured to move together with the drive member and the shaft along the predetermined rotation axis, the interlocking member being configured to engage with the receiver while the end effector is bent relative to the shaft, thereby preventing rotation of the shaft and the drive member around the predetermined rotation axis relative to the housing.

2. The treatment instrument according to claim 1,
   wherein the drive member extends along the predetermined rotation axis from an inside of the housing through an inside of the shaft, and
   wherein the interlocking member is configured to engage with the receiver in the inside of the housing while the end effector is bent relative to the shaft, the receiver being provided in such a manner that the rotation of the receiver relative to the housing is restricted.

3. The treatment instrument according to claim 2,
   wherein a slot is formed in the shaft to communicate the inside of the shaft with an outside of the shaft, and
   wherein the interlocking member is inserted into the shaft through the slot, and engages with the receiver on the outside of the shaft while the end effector is bent relative to the shaft.

4. The treatment instrument according to claim 1,
   wherein the shaft includes a first abutting surface, and the receiver is provided in a such manner that the rotation of the receiver relative to the shaft is restricted, the shaft being configured to engage with the receiver, thereby the shaft moving along the predetermined rotation axis relative to the housing, and
   wherein the housing includes a second abutting surface against which the first abutting surface abuts in correspondence with movement of the shaft relative to the housing, and the first abutting surface abuts against the second abutting surface so as to prevent the rotation of the shaft and the drive member around the predetermined rotation axis relative to the housing.

5. The treatment instrument according to claim 1, further comprising:
   an operation input member at which an operation of bending the end effector relative to the shaft is input; and
   an operation force transmitter configured to transmit an operation force for bending the end effector by being activated based on an operation input at the operation input member.

6. The treatment instrument according to claim 5,
   wherein the operation input member and the operation force transmitter rotate together with the shaft around the predetermined rotation axis by a rotation drive force transmitted from the shaft upon rotation of the shaft around the predetermined rotation axis, and wherein the receiver is provided in such a manner that the rotation of the receiver relative to the housing is restricted, and the interlocking member is configured to engage with the receiver, thereby preventing rotation of the operation input member and the operation force transmitter around the predetermined rotation axis relative to the housing, the engagement of the interlocking member with the receiver being achieved by moving the interlocking member in conjunction with the operation input at the operation input member and in conjunction with an activation of the operation force transmitter based on the operation input.

7. The treatment instrument according to claim 6, further comprising a drive member configured to move along the predetermined rotation axis by the operation force transmitted from the operation force transmitter, thereby bending the end effector relative to the shaft, the drive member being configured to rotate together with the shaft, the operation input member, and the operation force transmitter around the predetermined rotation axis.

8. The treatment instrument according to claim 5, wherein the receiver is provided in such a manner that the rotation of the receiver relative to the shaft is restricted, and the interlocking member is configured to engage with the receiver, thereby preventing the rotation of the shaft around the predetermined rotation axis relative to the operation input member and the operation force transmitter, the engagement of the interlocking member with the receiver being achieved by moving the interlocking member in conjunction with the operation input at the operation input member and in conjunction with an activation of the operation force transmitter based on the operation input.

9. The treatment instrument according to claim 8, further comprising a drive member configured to move along the predetermined rotation axis by the operation force transmitted from the operation force transmitter, thereby bending the end effector relative to the shaft, the drive member being configured to rotate together with the shaft around the predetermined rotation axis relative to the operation input member and the operation force transmitter.

10. A treatment instrument comprising:
a holdable housing;
a shaft rotatable around a predetermined rotation axis relative to the housing;
an end effector attached to a distal portion of the shaft, and bendable relative to the shaft;
a bending drive member configured to transmit an operation force for bending the end effector, the bending drive member configured to move along the predetermined rotation axis so as to bend the end effector relative to the shaft, the bending drive member being rotatable together with the shaft around the predetermined rotation axis;
an interlocking member stationarily fixed to the drive member and provided to move together with the bending drive member; and
a receiver configured to engage with the interlocking member so as to prevent the shaft from rotating around the predetermined rotation axis while the end effector is bent,
wherein the interlocking member is configured to move together with the bending drive member and the shaft along the predetermined rotation axis, the interlocking member being configured to engage with the receiver while the end effector is bent relative to the shaft, thereby preventing rotation of the shaft and the bending drive member around the predetermined rotation axis relative to the housing.

* * * * *